United States Patent
Maxwell et al.

(10) Patent No.: US 10,004,485 B2
(45) Date of Patent: Jun. 26, 2018

(54) SURGICAL INSTRUMENT FOR DISPENSING A FLUID

(71) Applicant: SURGICAL INNOVATIONS LIMITED, Leeds, Yorkshire (GB)

(72) Inventors: Vhairi Maxwell, Leeds (GB); Keir Ridler, Leeds (GB)

(73) Assignee: Surgical Innovations Limited, Leeds, Yorkshire (GB)

( * ) Notice: Subject to any disclaimer, the term of this patent is extended or adjusted under 35 U.S.C. 154(b) by 364 days.

(21) Appl. No.: 14/441,058

(22) PCT Filed: Nov. 1, 2013

(86) PCT No.: PCT/GB2013/052872
§ 371 (c)(1),
(2) Date: May 6, 2015

(87) PCT Pub. No.: WO2014/072689
PCT Pub. Date: May 15, 2014

(65) Prior Publication Data
US 2015/0297207 A1 Oct. 22, 2015

(30) Foreign Application Priority Data

Nov. 7, 2012 (GB) .................................. 1220089.5
Nov. 7, 2012 (GB) .................................. 1220090.3

(51) Int. Cl.
*A61B 17/00* (2006.01)
*A61M 5/31* (2006.01)
(Continued)

(52) U.S. Cl.
CPC .... *A61B 17/00491* (2013.01); *A61B 17/8805* (2013.01); *A61B 17/8822* (2013.01);
(Continued)

(58) Field of Classification Search
CPC .... A61B 2017/00495; A61B 2017/005; A61B 2017/00504; A61B 2017/00508;
(Continued)

(56) References Cited

U.S. PATENT DOCUMENTS

2004/0254561 A1  12/2004  Stenton
2006/0049203 A1   3/2006  Boone et al.
(Continued)

FOREIGN PATENT DOCUMENTS

WO   WO 99/39666 A1   8/1999
WO   WO 02/64192 A1   8/2002
(Continued)

*Primary Examiner* — Todd J Scherbel
(74) *Attorney, Agent, or Firm* — Edwin D. Schindler

(57) ABSTRACT

A surgical instrument for dispensing a fluid includes a housing and a dispensing shaft. The surgical instrument further includes a dispensing assembly connected to the housing, which includes a dispensing chamber for holding the fluid before it is dispensed. A container is included in which the fluid is stored before the surgical instrument is used. A transfer assembly is included and is connected to the housing which is operable to open the container and transfer the fluid from the opened container to the dispensing chamber before the dispensing assembly is operated.

17 Claims, 20 Drawing Sheets

(51) Int. Cl.
*A61B 17/88* (2006.01)
*A61B 90/00* (2016.01)

(52) U.S. Cl.
CPC . *A61M 5/3146* (2013.01); *A61B 2017/00367* (2013.01); *A61B 2017/00495* (2013.01); *A61B 2090/0814* (2016.02); *A61B 2090/08021* (2016.02)

(58) Field of Classification Search
CPC   A61B 2017/00513; A61B 2017/00517; A61B 2017/00522; A61B 2017/8813; A61B 2017/8816; A61B 2017/8819; A61B 2017/8822; A61B 2017/8825; A61B 17/00491; A61B 17/8802; A61B 17/8805; A61M 5/3146
See application file for complete search history.

(56) References Cited

U.S. PATENT DOCUMENTS

2009/0247985 A1\* 10/2009  Melsheimer ..... A61B 17/12022
                                                                  604/506
2015/0297206 A1\* 10/2015  Maxwell ............ A61B 17/8822
                                                                  606/214

FOREIGN PATENT DOCUMENTS

| WO | WO 02/064192  | A1 | 8/2002 |
| WO | WO 2006/032070 | A1 | 3/2006 |
| WO | WO 2008/103296 | A1 | 8/2008 |
| WO | WO 2009/132331 | A1 | 4/2009 |
| WO | WO 2010/145041 | A1 | 12/2010 |

\* cited by examiner

SURGICAL INSTRUMENT FOR DISPENSING A FLUID

BACKGROUND OF INVENTION

Technical Field of the Invention

The present invention relates to a surgical instrument for dispensing a fluid. In particular the invention may relate to a surgical instrument for dispensing a fluid to an operative site in the human or animal body.

Description of Prior Art

Surgical instruments for dispensing fluid to an operative site in the human or animal body are known. WO2009/132331 discloses a minimally invasive (e.g. laparoscopic) applicator device which dispenses fluid and which may include a ratcheted trigger system to overcome backflow. WO02/064192 discloses a laparoscopic gel applicator. However, the applicant has recognised that the devices disclosed in these documents may not be suitable for use with fluids which are stored before use in a container made from a material which may fragment when the container is opened.

SUMMARY OF THE INVENTION

The present invention seeks to provide a surgical instrument for dispensing fluid which is suitable for use with a fluid which is stored in a frangible container before use.

Thus viewed from one aspect the present invention provides a surgical instrument for dispensing a fluid comprising:
  a housing;
  a dispensing shaft which is elongate and which has a proximal end and a distal end, wherein the proximal end of the dispensing shaft is received in the housing and the distal end defines a dispensing opening for dispensing the fluid and the dispensing shaft includes a through bore which extends along the dispensing shaft from the proximal end to the dispensing opening at the distal end;
  a dispensing assembly connected to the housing which includes a dispensing chamber which holds the fluid before it is dispensed, wherein the dispensing chamber is in fluid communication with the through bore of the dispensing shaft and the dispensing assembly is operable to move the fluid from the dispensing chamber along the through bore and dispense the fluid from the dispensing opening;
  a container in which the fluid is stored before the surgical instrument is used; and
  a transfer assembly connected to the housing which is operable to open the container and transfer the fluid from the opened container to the dispensing chamber before the dispensing assembly is operated.

By providing a transfer assembly, the surgical instrument may advantageously be suitable for use with a fluid which is stored in a frangible container before use. This is because the provision of a transfer assembly between the container and the dispensing chamber may prevent any fragments of the opened container from reaching the dispensing chamber.

The container may be made of a frangible material. An example of a frangible material is glass. The container may be a frangible container.

The container may be made of a material which during deformation tends to break up into fragments, rather than deforming plastically and remaining in one piece.

The housing may comprise a handle. The handle may allow the surgical instrument to be gripped in one hand to allow one-handed operation of the surgical instrument. The housing may comprise a body. The dispensing shaft may extend from the body. The housing may have a 'pistol' configuration in which the handle extends from the body in a similar configuration to a pistol handle extending from a pistol barrel.

The dispensing shaft is elongate and has a proximal end and a distal end. The proximal end of the dispensing shaft is received within the housing and the distal end defines a dispensing opening for dispensing the fluid. The dispensing shaft may have a longitudinal axis. The longitudinal axis of the dispensing shaft may define a proximo-distal axis for the surgical instrument. The proximo-distal axis may be oriented so that the distal direction is generally towards the distal end of the dispensing shaft and the proximal direction is generally away from the distal end.

The dispensing shaft may comprise an inner tube and an outer tube. The outer tube may be made of metal. The inner tube may be made of a polymer. The polymer may be polytetrafluoroethylene (PTFE), fluorinated ethylene propylene (FEP) or silicone. The polymer may be a non-stick or low friction polymer. This may assist the movement of the fluid along the through bore by reducing shear stress. For example, when the fluid is an adhesive or has a significant viscosity, a non-stick or low friction polymer may assist the flow of the fluid along the through bore.

The through bore may be defined within the inner tube.

The dispensing assembly comprises a dispensing chamber. The fluid may be held in the dispensing chamber before it is moved into the dispensing shaft. An elongate plunger may be positioned to advance or retract within the dispensing chamber. When the plunger is advanced within the dispensing chamber, the fluid may be urged out of the dispensing chamber and into the dispensing shaft. The plunger may advance within the dispensing chamber in a distal direction. Fluid urged out of the dispensing chamber may enter the through bore of the dispensing shaft at the proximal end of the dispensing shaft.

The plunger may engage the internal surface of the dispensing chamber to form a seal. Alternatively the plunger may abut against a sealing disc which engages the internal surface of the dispensing chamber to form a seal. Advancement of the plunger may advance the sealing disc within the chamber. The plunger may include a proximal end and a distal end. The distal end of the plunger may abut the sealing disc.

Preferably the plunger abuts against a sealing disc which is slidably mounted within the dispensing chamber, wherein operation of the dispensing assembly causes the plunger to advance the sealing disc within the dispensing chamber to urge the fluid out of the dispensing chamber and along the through bore in the dispensing shaft.

The plunger may be connected to a plunger drive assembly. The plunger drive assembly may be a rack and pinion. The rack may be mounted on the plunger. The pinion gear wheel may be mounted within the housing. Turning the pinion gear wheel may engage the rack to advance or retract the plunger along the dispensing chamber.

The dispensing assembly may comprise a dispensing actuator. The dispensing actuator may be operable to drive the dispensing assembly. The dispensing actuator may be reciprocable between a first dispensing position and a second dispensing position. Movement of the dispensing actuator from the first dispensing position to the second dispensing position may advance the plunger and urge fluid out of» the dispensing chamber and along the dispensing shaft. The dispensing actuator may be biased to return to the first dispensing position when it is released at the second dispensing position.

The dispensing actuator may be connected to the plunger drive assembly. For example, the dispensing actuator may be connected by an intermediate gear wheel to the pinion gear of the plunger drive assembly.

The dispensing actuator may be a trigger. The trigger may be reciprocable. The trigger may be mounted to the housing. The trigger may be mounted to the handle or the body of the housing. The trigger may be operable by a user's finger from a first trigger position to a second trigger position. The trigger may be biased by a spring to return to the first trigger position when the user's finger is released at the second trigger position. The spring may be attached to the housing at a first end and attached to the trigger at a second end.

Preferably the dispensing assembly includes a trigger mounted to the housing which is operable to dispense a predetermined amount of fluid each time the trigger is operated.

A pawl and ratchet may be connected to the trigger and a trigger gear wheel. The pawl may be connected to one of the trigger or the trigger gear wheel and the ratchet may be connected to the other of the trigger or the trigger gear wheel. The pawl may be moulded into the trigger. When the trigger is moved from the first trigger position to the second trigger position the pawl may engage the ratchet to turn the trigger gear wheel. When the trigger is moved from the second trigger position to the first trigger position the pawl and ratchet may disengage so that the trigger gear wheel does not turn.

Turning the trigger gear wheel may turn the pinion gear wheel to advance the plunger. An intermediate gear wheel may be connected between the trigger gear wheel and the pinion gear wheel. The relative sizes of the trigger gear wheel and pinion gear wheel may be chosen to provide a suitable gear reduction. This may provide a mechanical advantage to the operation of the trigger from the first trigger position to the second trigger position. The intermediate gear may contribute to the gear reduction. The overall gear ratio between the trigger gear wheel and the pinion gear wheel may be 4 to 1. Therefore a 10° rotation of the trigger may result in a 2.5° rotation of the pinion gear wheel. The size of the pinion gear wheel may be chosen to advance the rack by a predetermined amount when the trigger is operated from the first trigger position to the second trigger position. This will cause the plunger to advance by a predetermined amount to dispense a predetermined volume of the fluid.

An indexing wheel may be attached to the trigger gear wheel. The indexing wheel may enable the movement of the trigger between the first trigger position and the second trigger position to be indexed. The indexing wheel may include indentations on its circumference which engage an indexing formation on the housing to provide the indexing. The engagement of the indentations with the indexing formation may also provide an additional frictional force on the ratchet to assist the trigger to move from the second trigger position to the first trigger position without moving the ratchet.

The surgical instrument may include a priming assembly connected to the housing which is operable to move an amount of the fluid into the through bore of the dispensing shaft to prime the through bore with the fluid before the dispensing assembly is operated.

By including a priming assembly, the likelihood of accidental dispensing of fluid by a user of the surgical instrument may advantageously be reduced because the fluid will not be present in the through bore until the priming assembly is operated to prime the through bore with the fluid. In this way operation of the dispensing assembly will not dispense fluid from the dispensing opening until the priming assembly has been operated. Reducing the likelihood of accidental dispensing of fluid is advantageous because fluid may be dispensed in an undesirable location. For example, if the fluid is an adhesive, accidentally dispensed adhesive may contact unintended tissue in the human or animal body which may be undesirable.

Operation of the priming assembly may prepare the surgical instrument for use. The priming assembly may comprise a priming actuator. The priming actuator may be operable to drive the priming assembly. The priming actuator may be mounted to a proximal end of the housing. The priming actuator may be rotatably mounted to the housing. The priming actuator may be operable from a first priming position to a second priming position. The priming actuator may be rotatable from the first priming position to the second priming position.

The priming assembly may include a safety element which is moveable from an engaged position to a disengaged position. The safety element may prevent the priming assembly from being operated when it is in the engaged position. The safety element may be in the form of a pull tab connected to the priming actuator. In its engaged position, the pull tab may engage a recess on the housing to prevent the priming actuator from being operated from the first priming position to the second priming position. The pull tab may be separable from the priming actuator so that in its disengaged position, the pull tab is separated from the priming actuator and disengaged from the recess so that the priming actuator can be operated.

Operation of the priming actuator may cause the plunger to advance into the dispensing chamber. The plunger may advance in a distal direction.

If the priming actuator is rotatably mounted to the housing, rotation of the priming actuator may rotate a priming cap with an internal screw thread. The priming cap may be linearly moveable with respect to the priming actuator by the engagement of a spline feature on one of the priming cap or the priming actuator with a groove on the other of the priming cap or priming actuator. The internal screw thread on the priming cap may engage a complementary screw thread mounted on the plunger drive assembly. The priming cap may be connected to the proximal end of the plunger. In this way, rotation of the priming actuator may cause the internal screw thread on the priming cap to advance along the complementary screw thread on the plunger drive assembly. Since the plunger is connected to the priming cap, the plunger will advance distally with respect to the plunger drive assembly. The advancement of the plunger may prime the through bore of the dispensing shaft with fluid by advancing the sealing disc in the dispensing chamber and urging the fluid out of the dispensing chamber.

The priming assembly and the dispensing assembly may form an interlock so that the dispensing assembly cannot be operated until the priming assembly has been operated. The interlock may be moveable from a locked configuration in which it prevents the dispensing assembly from being operated to a released configuration in which the dispensing assembly is operable. The interlock may only be moveable to the released configuration once the priming actuator is in the second priming position. An advantage of the interlock may be that accidental operation of the dispensing assembly is not possible until the priming assembly has been operated and the priming actuator is in the second priming position.

The interlock may include a locking member. The locking member may be elongate and may be moveably mounted in the housing to contact a locking formation on the dispensing assembly and to contact the priming actuator. When the priming actuator is in the first priming position and the interlock is in the locked configuration, the locking member may be unable to move and may lock the trigger in the second trigger position by contact with the locking formation.

The priming actuator may include an interlock recess positioned so that when the priming actuator is in the second priming position, the interlock recess is aligned with the locking member to allow the locking member to move into the interlock recess. The spring bias on the trigger may then cause the locking formation to move the locking member into the interlock recess and this released configuration allows the trigger to move from the second trigger position to the first trigger position. Once the trigger is in the first trigger position, it is operable by the user.

Preferably the priming assembly includes a priming actuator which is operable from a first priming position to a second priming position and which includes an interlock recess; and the interlock includes a locking member which is able to enter the interlock recess when the priming actuator in the second priming position to release the interlock and allow the dispensing assembly to be operated.

The fluid may be a medical fluid. The fluid may be a liquid or a gel. The fluid may aid in the recovery or the comfort of the patient. The fluid may have a viscosity similar to water at room temperature. The fluid may have a higher viscosity than water at room temperature. The fluid may be a pharmaceutical agent, hemostatic solution, wound-healing agent, analgesic, anti-adhesive, adhesive, irrigation fluid or cooling fluid. The fluid may include an anesthetic, an antibiotic in fluid form, a growth factor, suspended stem cells, chondrocytes, other biologically active substances such as extracellular matrix, including proteoglycans, glycosaminoglycan (GAG), chondroitin sulfate, or an antihemorragic.

The fluid may be a bone cement.

The fluid may be an adhesive. The adhesive may be a collagen-based adhesive, a hydrogel, an albumin-based compound, a cyanoacrylate or a fibrin.

The fluid may be a cyanoacrylate adhesive. The cyanoacrylate adhesive may have a viscosity similar to water at room temperature.

In another embodiment, the fluid may be a fibrin adhesive. The fibrin adhesive may be a binary mixture in which two inactive precursor fluids are mixed to form the active fibrin adhesive.

The surgical instrument may include a first container for a first precursor fluid and a second container for a second precursor fluid. The dispensing assembly may comprise a first dispensing chamber for the first precursor fluid and a second dispensing chamber for the second precursor fluid. The dispensing assembly may include a first plunger for the first dispensing chamber and a second plunger for the second dispensing chamber. The first and second plungers may be advanced by a common plunger drive assembly. A mixing chamber may be located between the first and second dispensing chambers and the dispensing shaft. The first and second precursor fluids may mix in the mixing chamber to form the active fibrin adhesive before moving into the dispensing shaft.

To ensure sterility and prolong shelf-life, the fluid may be stored in a glass container. The container may be a glass ampoule. When the fluid is a cyanoacrylate adhesive, the cyanoacrylate adhesive may be stored in a sealed glass container to prevent contact with moisture which may cause the cyanoacrylate adhesive to polymerise.

A polymer sleeve may at least partially surround the container. The polymer sleeve may be a PTFE sleeve. When the container is opened, the polymer sleeve may prevent the fluid from spilling out of the container holder.

The transfer assembly may include a filter which is positioned between the container and the dispensing chamber for separating fragments of the container which may be produced when the container is opened from the fluid which is transferred to the dispensing chamber. An advantage of this configuration is that it ensures that fluid which is transferred to the dispensing chamber is free from container fragments.

Preferably the transfer assembly includes a filter which is positioned between the container and the dispensing chamber for retaining fragments of the frangible container which may be produced when the container is opened and separating the fragments from the fluid which is transferred to the dispensing chamber.

The apertures of the filter may be sized to allow the fluid to pass but to retain any fragments of the container which are produced when the container is opened.

The transfer assembly may include a container holder which holds the container. The container holder may include the filter.

The dispensing chamber may be attached to the transfer assembly.

A sealing disc in the dispensing chamber may be engaged by the plunger once the priming assembly has been operated. Advancement of the plunger may cause the sealing disc to advance in the dispensing chamber.

The transfer assembly may be moveably mounted to the housing. The transfer assembly may pivot with respect to the housing. The transfer assembly may be moveable between a first transfer position, a second transfer position and a third transfer position.

Movement of the transfer assembly from the first transfer position to the second transfer position may cause the container to be opened to release the fluid. The container may be opened by a projection on the transfer assembly being pushed into the container. When the container is a frangible container, this will break open the frangible container. Any container fragments created by the opening of the container may be retained by the filter.

The projection may be pushed into the container by relative movement of the container holder with respect to the projection. The transfer assembly may include a breaker section which is moveable with regard to a holder section. The projection may be located on the breaker section and the container holder may attached to the holder section. When the transfer assembly is moved from the first transfer position to the second transfer position, the holder section may move relative to the breaker section. For example, the breaker section may be moveably retained on the housing so that it cannot move as far as the holder section. In this way, moving the holder section to its maximum extent will move the holder section relative to the breaker section.

Once the fluid is released from the container, it may be directed to the dispensing chamber. A valve may be positioned between the container and the dispensing chamber. The valve may comprise an outer valve body and an inner valve member. The valve may be a plug valve. The valve member may be a cylinder with a cylindrical surface and axial ends. The valve body may be annular and encircle the valve member. The valve member may be attached to the housing at its axial ends and the valve body may be attached to the transfer assembly. In this way the valve member may act as a pivot around which the valve body and transfer assembly rotates when the transfer assembly moves between the first transfer position, second transfer position and third transfer position. This use of the valve member as a pivot for the transfer assembly may advantageously reduce the number of components required in the surgical instrument.

Preferably the transfer assembly is moveable to a third transfer position and the surgical instrument includes a valve which is positioned between the container and the dispensing chamber wherein in the second transfer position the valve allows fluid to flow from the container into the dispensing chamber and wherein in the third transfer position the valve allows fluid to flow from the dispensing chamber into the dispensing shaft.

Preferably the valve includes an outer valve body and an inner valve member, wherein the valve body is attached to the transfer assembly and the valve member is attached to the housing so that the valve body is rotatable around the valve member to allow the transfer assembly to rotate between the first transfer position, second transfer position and third transfer position.

Preferably the valve member is cylindrical and the valve body is annular and encircles the valve member so that the valve member acts as a pivot around which the valve body and transfer assembly are rotatable.

A transfer channel may be defined by the valve member. When the valve member is a cylinder, the transfer channel may be a channel on its cylindrical surface. The valve body may define a container holder opening which is in fluid communication with the container holder. The valve body may define a dispensing chamber opening which is in fluid communication with the dispensing chamber.

The valve member may further define a dispensing channel. The dispensing channel may be a diametrical channel through the valve member.

When the transfer assembly is in the first transfer position, the transfer channel may not be aligned with the container holder opening and the dispensing chamber opening. When the transfer assembly is in the second transfer position, the transfer channel may be aligned with the container holder opening and the dispensing chamber opening to provide a fluid path between the container holder opening and the dispensing chamber opening. In this way, fluid released from the container may flow from the container holder to the dispensing chamber when the transfer assembly is in the second transfer position.

Before the surgical instrument is used, the sealing disc may be located at a distal end of the dispensing chamber. To draw the released fluid through the transfer channel from the container holder when the transfer assembly is in the second transfer position, the sealing disc may be retracted proximally in the dispensing chamber. A pull member may be attached to the sealing disc to allow the user to retract the sealing disc. When the transfer assembly is in the first transfer position, the pull member may be restrained from movement by the housing. When the transfer assembly is moved from the first transfer position to the second transfer position, the pull member may move above the housing so that it is no longer restrained. In this way the pull member cannot be operated accidentally before the container has been opened by movement of the transfer assembly from the first transfer position to the second transfer position.

Preferably the pull member is attached to the sealing disc and the pull member is operable to retract the sealing disc within the dispensing chamber to draw the fluid from the opened container into the dispensing chamber when the transfer assembly is in the second transfer position and before the dispensing assembly is operated.

Preferably the pull member is located in a position so that before it is operated and when the transfer assembly is in the first transfer position, the pull member is restrained from movement by the housing to prevent the pull member from being operated until the transfer assembly is in the second transfer position and the container has been opened.

Before the pull member is operated to retract the sealing disc within the dispensing chamber to draw the fluid from the opened container into the dispensing chamber, it may be located in a position which prevents the transfer assembly from being moved from the second transfer position to the third transfer position. In this way the transfer assembly cannot be moved accidentally to the third transfer position before the pull member has been operated.

Once all the fluid has been drawn into the dispensing chamber and the sealing disc is fully retracted, the pull member may disengage from the sealing disc. The pull member may comprise two fingers which engage a recess on the sealing disc so that the sealing disc may be retracted. The sealing disc may be in the form of a through-hole. The fingers may be retained in the recess by the inner surface of the dispensing chamber. At its proximal end, the dispensing chamber may define two slots which allow the fingers to disengage from the recess when the sealing disc is fully retracted. In this way, the pull member is disengaged and separated from the dispensing chamber and may be discarded.

Preferably the pull member includes disengageable fingers which engage the sealing disc so that when the pull member has been operated to retract the sealing disc within the dispensing chamber, the fingers are disengageable from the sealing disc to allow the pull member to be moved to a position which allows the transfer assembly to be moved from the second transfer position to the third transfer position.

After the pull member is discarded, the sealing disc may be fully retracted and the dispensing chamber contains the fluid to be dispensed. The transfer assembly may then be moved to the third transfer position. To reach the third transfer position, the transfer assembly may be pivoted about the valve member until the dispensing chamber opening is aligned with the dispensing channel. When the transfer assembly is in the third transfer position, the sealing disc may be aligned with the plunger. The priming actuator may then be operated. When the priming actuator is operated from the first priming position to the second priming position, the plunger may advance the sealing disc distally within the dispensing chamber and push the fluid through the dispensing chamber opening and the dispensing channel. The proximal end of the dispensing shaft may be received within the valve member and the through bore may be connected to the dispensing channel. Therefore fluid pushed through the dispensing channel may travel distally along the through bore and be dispensed from the dispensing opening at the distal end of the dispensing shaft.

The fluid may be dispensed in discrete doses. Each dose may be a predetermined amount of fluid. A single dose may be known as a delivery. Each delivery may be of a predetermined volume. The dimensions of the dispensing chamber and plunger may be configured so that advancement of the plunger by a set distance dispenses the predetermined volume.

The predetermined volume of a delivery may be up to 50 mm$^3$. The predetermined delivery volume may be from 10 mm$^3$ to 40 mm$^3$. Preferably the predetermined delivery volume is from 20 mm$^3$ to 30 mm$^3$, more preferably the predetermined delivery volume is approximately 25 mm$^3$.

If the predetermined delivery volume is approximately 25 mm$^3$ and the internal diameter of the dispensing chamber is 7 mm, the plunger will advance approximately 0.65 mm for each separate delivery of fluid.

The surgical instrument may be capable of dispensing a predetermined number of deliveries. The predetermined number of deliveries may be up to 50 deliveries. Preferably the predetermined number of deliveries is from 20 to 50 deliveries, more preferably from 30 to 40 deliveries. The predetermined number of deliveries may be 35 deliveries.

After the dispensing actuator has been operated for a number of times equal to the predetermined number of deliveries, a hard stop on the dispensing assembly may prevent the dispensing actuator from being operated again. The hard stop may be provided by a stop projection on the plunger drive assembly engaging the housing.

The stop projection may be located in a slot on the housing. The slot may be in an exterior surface of the housing so that the stop projection is visible to the user of the surgical instrument. The stop projection may advance in the slot as the plunger advances the sealing disc in the dispensing chamber. The hard stop may be provided by the stop projection reaching an end of the slot. The slot may be located so that the stop projection reaches the end of the slot when the predetermined number of deliveries is reached.

By being visible to the user, the relative position of the stop projection in the slot may advantageously indicate the number of deliveries the surgical instrument has made. An indicator or scale may be marked on the housing to allow the user to judge the number of deliveries more accurately. For example, if the stop projection is located at a first end of the slot initially and reaches the second end of the slot when the predetermined number of deliveries is reached, then if the stop projection is in the middle of the slot, approximately half of the predetermined number of deliveries have been made.

The surgical instrument may be suitable for use in a minimally invasive surgical procedure. The surgical instrument may be suitable for hernia mesh fixation. The surgical instrument may be a hernia mesh fixation device.

When the surgical instrument is a hernia mesh fixation device, the fluid may be a cyanoacrylate adhesive for securing a hernia mesh in place at the operative site in the human or animal body. The hernia mesh may be secured in place by a number of deliveries of adhesive from the surgical instrument. Each delivery of adhesive may have a similar function to a suture or tack. The hernia mesh may be secured in place by between 20 and 30 deliveries of adhesive. The hernia mesh may be secured in place by approximately 25 deliveries of adhesive.

BRIEF DESCRIPTION OF THE DRAWING FIGURES

An embodiment of the invention will now be described by way of example only with reference to the accompanying drawings, in which like reference numerals indicate like parts and in which.

DETAILED DESCRIPTION OF THE DRAWING FIGURES AND PREFERRED EMBODIMENTS

Figure 1:
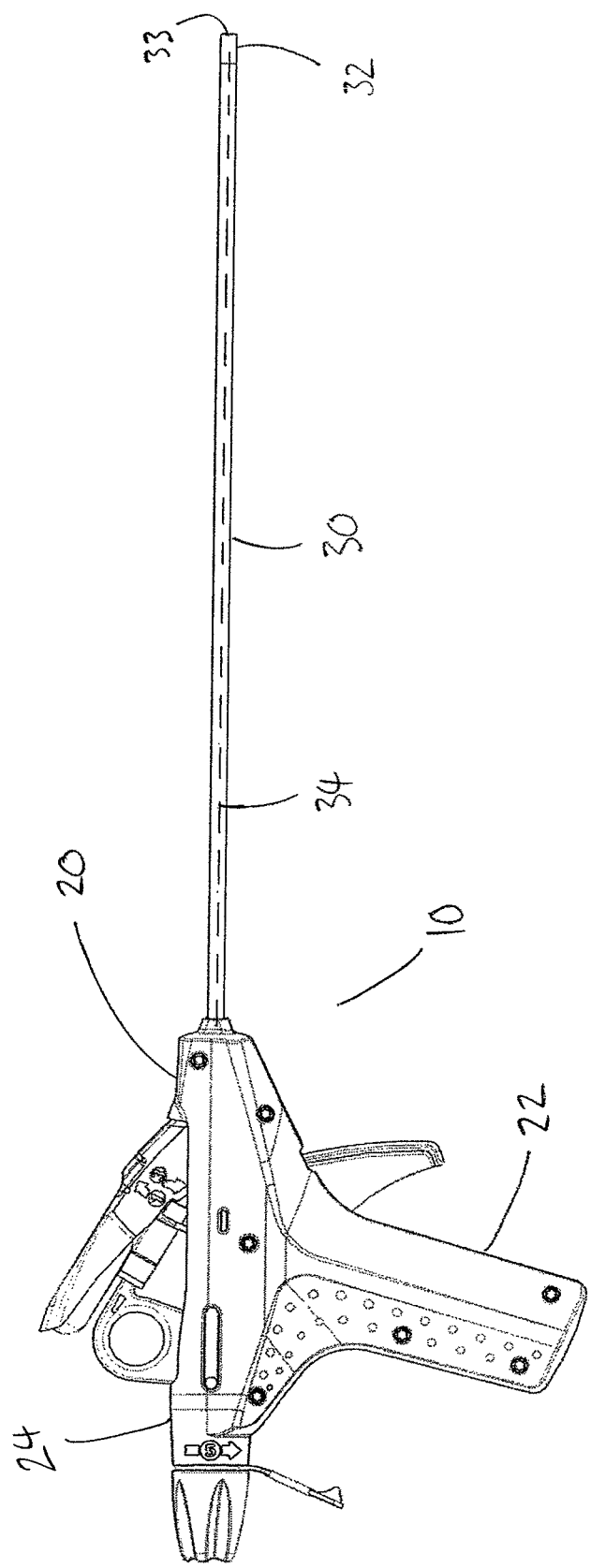
FIG. 1 is a view of the surgical instrument from the right hand side.

As shown in FIG. 1, the surgical instrument 10 comprises a housing 20 and a dispensing shaft 30.

The housing 20 comprises a handle 22 which allows the surgical instrument 10 to be gripped in one hand to allow one-handed operation of the surgical instrument 10. The housing 20 also comprises a body 24. The dispensing shaft 30 extends from the body 24. The housing 20 has a 'pistol' configuration in which the handle 22 extends from the body 24 in a similar configuration to a pistol handle extending from a pistol barrel.

Figure 2:
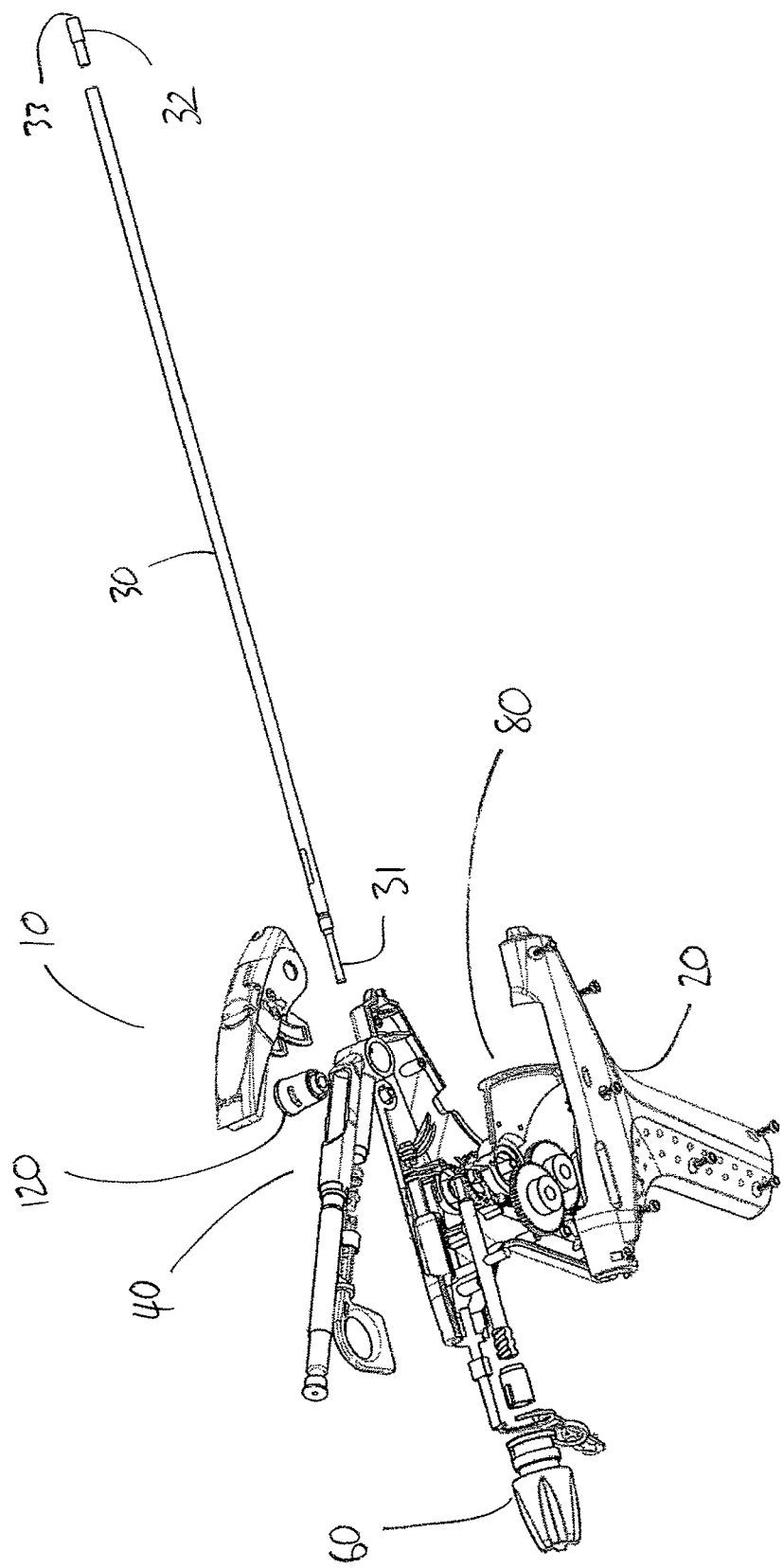
FIG. 2 is an exploded view of the surgical instrument from above the right hand side.
Figure 7:
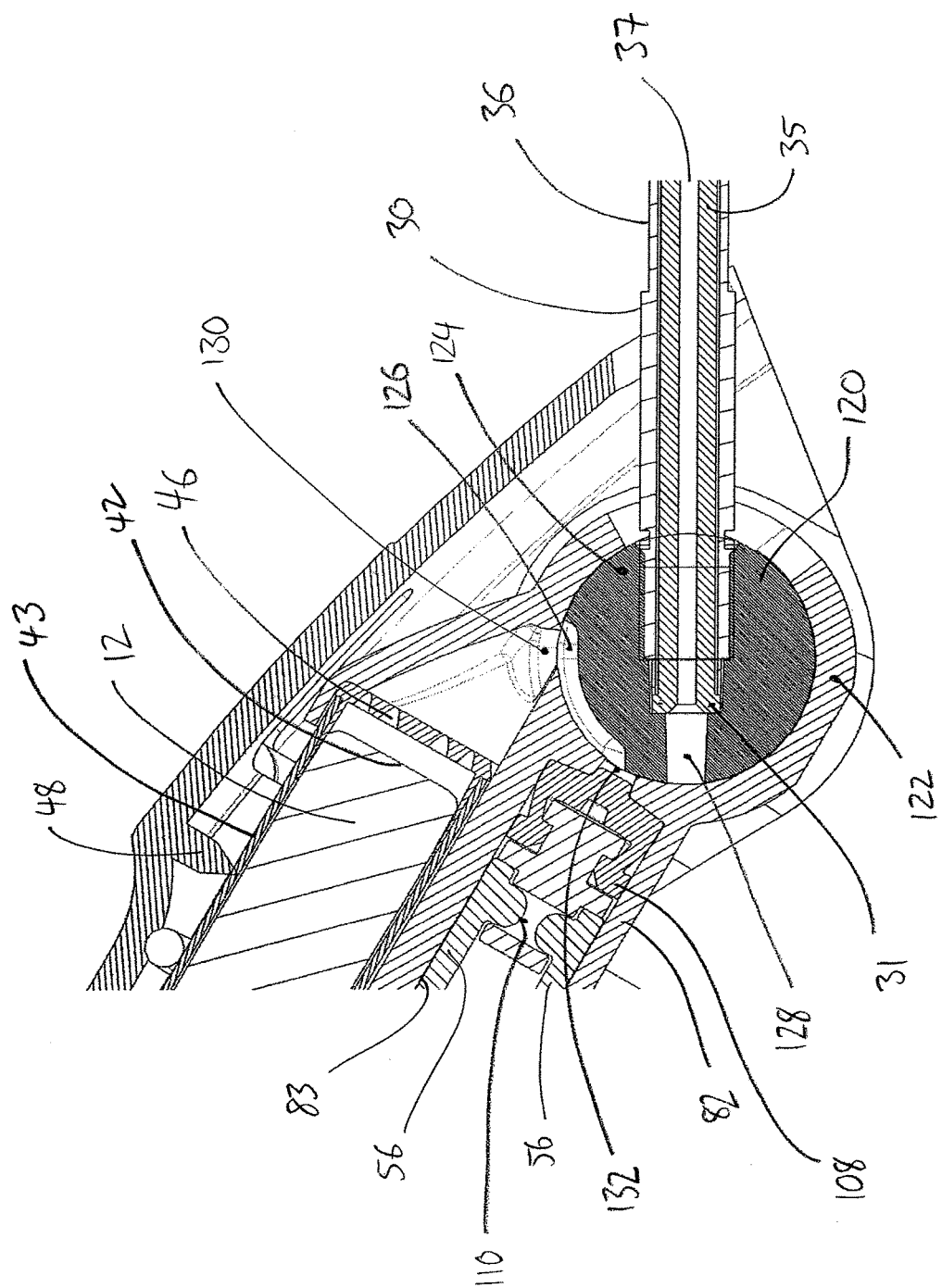
FIG. 7 is a magnified view of a part of FIG. 6.
Figure 14:
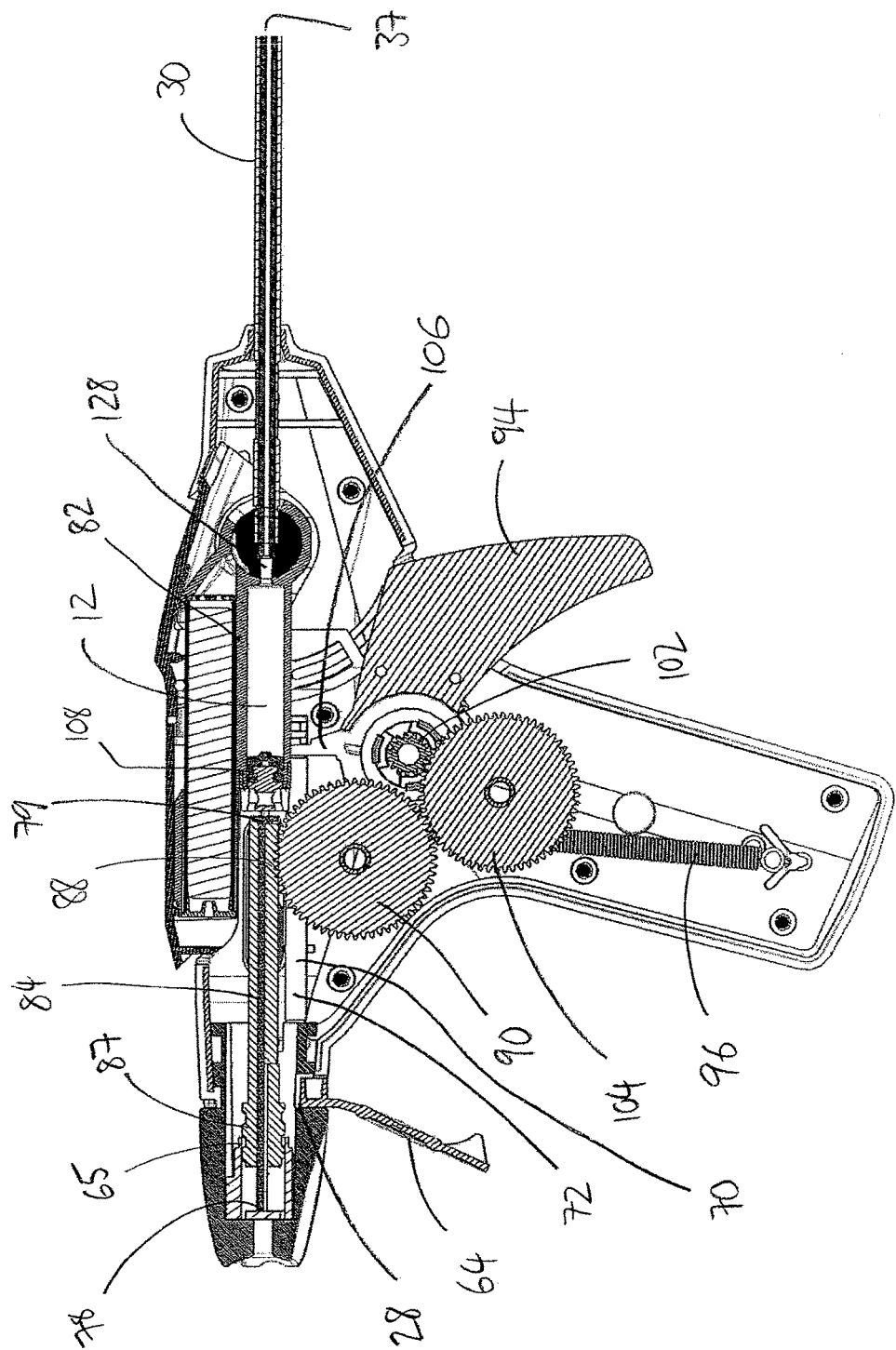
FIG. 14 is a cross-section of the surgical instrument from the right hand side showing the priming assembly in the first priming position.

As shown in FIGS. 1 and 2, the dispensing shaft 30 is elongate and has a proximal end 31 and a distal end 32. The proximal end 31 of the dispensing shaft 30 is received within the housing 20 and the distal end 32 defines a dispensing opening 33 for dispensing the fluid 12. The fluid 12 is shown in FIGS. 7 and 14. The dispensing shaft has a longitudinal axis 34 which defines a proximo-distal axis for the surgical instrument 10. The proximo-distal axis is oriented so that the distal direction is generally towards the distal end 32 of the dispensing shaft 30 and the proximal direction is generally away from the distal end 32.

As shown in FIG. 7, the dispensing shaft 30 comprises an inner tube 35 and an outer tube 36. The inner tube 35 defines a through bore 37 which allows the fluid 12 to pass along the dispensing shaft 30. The outer tube 36 is made of metal and the inner tube 35 is made of PTFE for low friction to assist the movement of the fluid 12 along the through bore 37 by reducing shear stress.

The fluid 12 is a cyanoacrylate adhesive with a viscosity similar to water at room temperature. To ensure its sterility, the fluid 12 is stored in a frangible glass container 42 before the surgical instrument 10 is used.

As shown in FIGS. 4 to 11, the surgical instrument 10 include a transfer assembly 40 which enables transfer of the fluid 12 from the container 42 to a dispensing chamber 82. The dispensing chamber 82 is attached to the transfer assembly 40.

The transfer assembly 40 is moveably mounted to the housing 20. The transfer assembly is moveable between a first transfer position (shown in FIGS. 3, 6 and 7), a second transfer position (not shown in the Figures) and a third transfer position (shown in FIGS. 9, 10 and 11).

The transfer assembly includes a container holder 44 which holds the container 42. The container holder includes a filter 46. The apertures of the filter 46 are sized to allow the fluid 12 to pass through the filter but to retain any fragments of the container 42 which are produced when the container 42 is opened. A PTFE sleeve 43 partially surrounds the container 42. When the container 42 is opened, the PTFE sleeve 43 prevents the fluid 12 from spilling out of the container holder 44.

Movement of the transfer assembly 40 from the first transfer position to the second transfer position causes the container 42 to be opened by a projection 48 on the transfer assembly 40 being pushed into the container 42 to break the wall of the container 42. Any glass fragments created by the opening of the container 42 will be retained by the filter 46.

The projection 48 is pushed into the container 42 by relative movement of the container holder 44 with respect to the projection 48. The transfer assembly 40 includes a breaker section 50 which is moveable with regard to a holder section 52. The projection 48 is located on the breaker section 50 and the container holder 44 is attached to the holder section 52.

Figure 3:
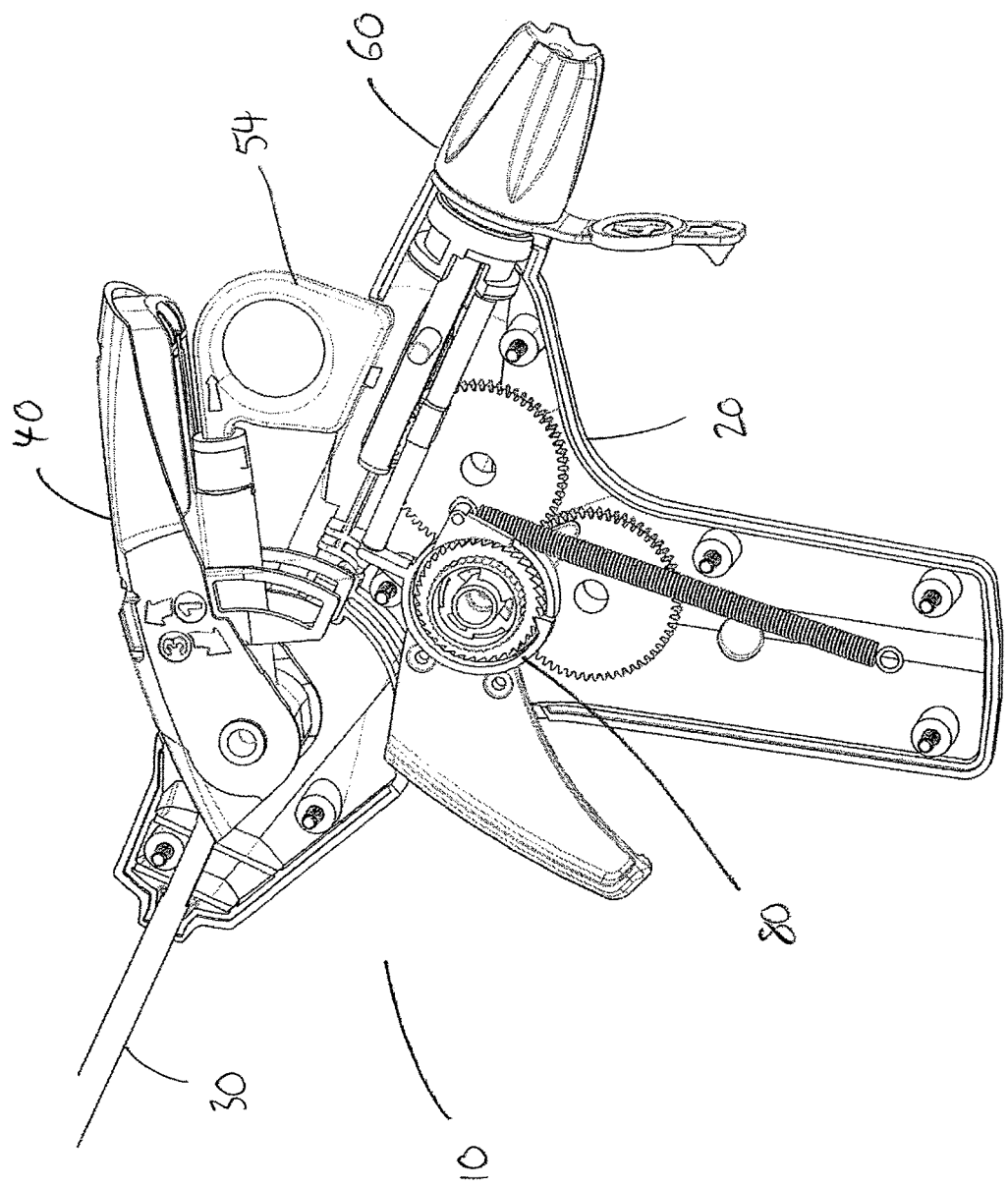
FIG. 3 is a view inside the housing of the surgical instrument from the left hand side.
Figure 4:
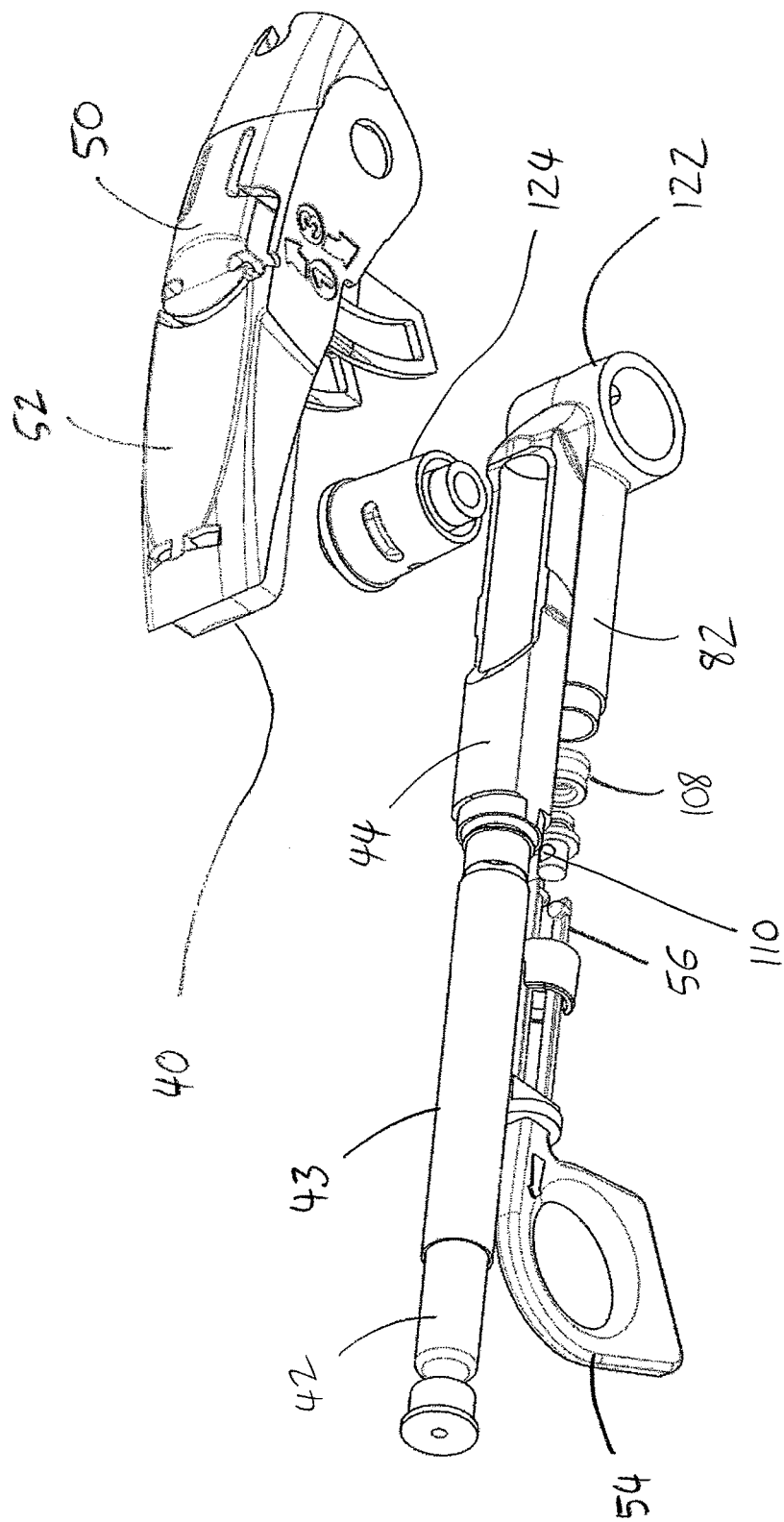
FIG. 4 is an exploded view of the transfer assembly of the surgical instrument.
Figure 5:
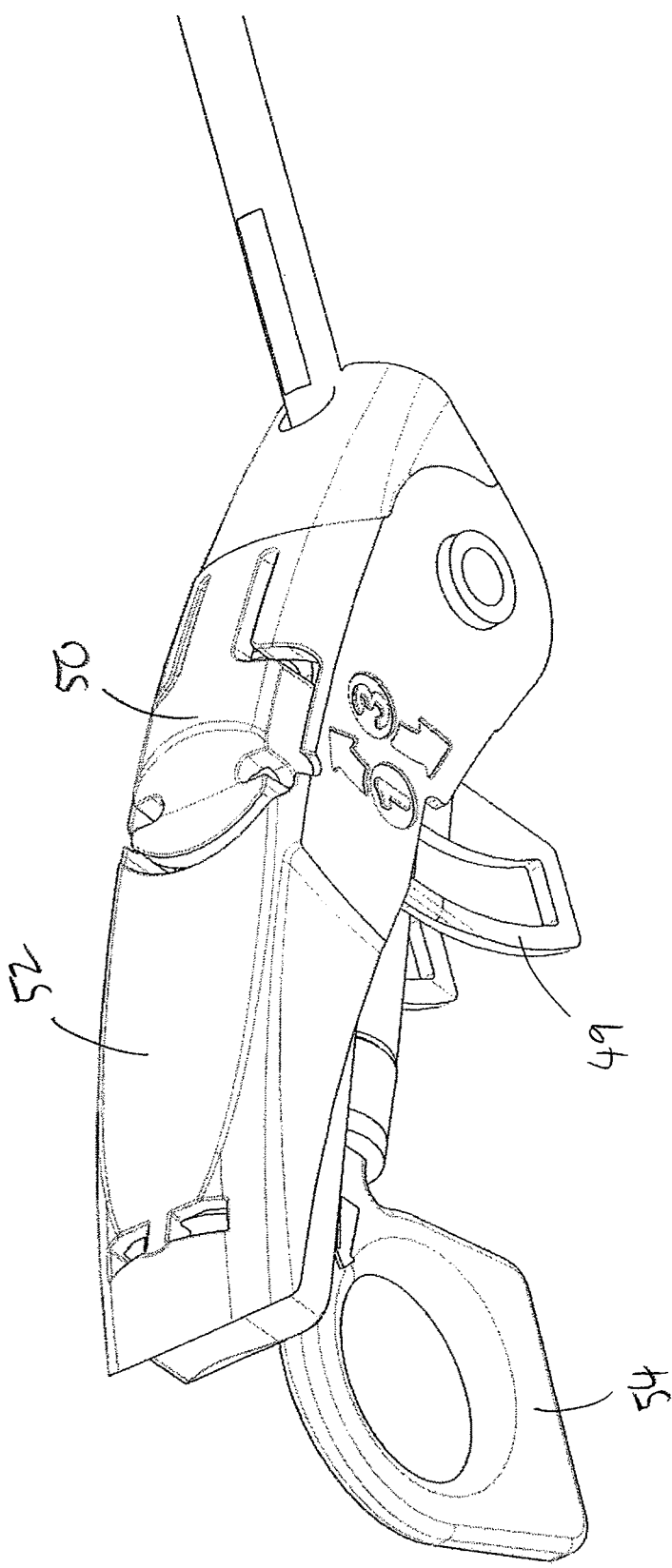
FIG. 5 is a view of the transfer assembly of the surgical instrument from the right hand side.
Figure 6:
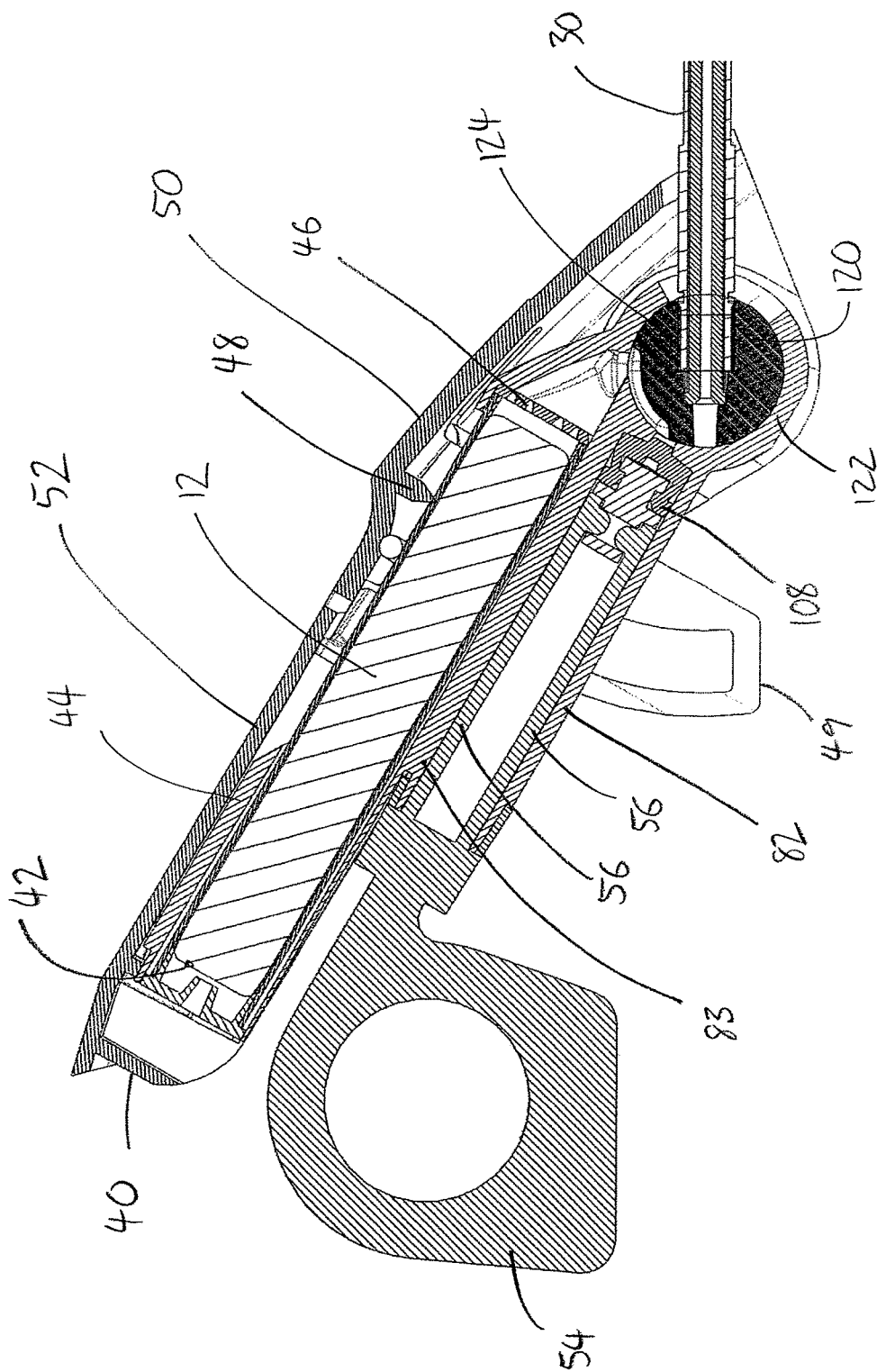
FIG. 6 is a cross-section of FIG. 5 showing the valve of the transfer assembly in the second transfer position.

In the first transfer position (as shown in FIGS. 3 and 6) the transfer assembly 40 is at an angle of approximately 25° to the longitudinal axis 34 of the dispensing shaft 30. When the transfer assembly 40 is moved from the first transfer position to the second transfer position, the holder section 52 is moved to an angle of approximately 35° to the longitudinal axis 34. The breaker section 50 is retained by the engagement of a hook member 49 with a catch 21 on the housing 20 (shown in FIG. 16) so that it cannot move further than 25° to the longitudinal axis 34. In this way, moving the holder section 52 to its maximum extent of approximately 35° will move the holder section 52 relative to the breaker section 50 and will cause the projection 18 to break open the container 42 and release the fluid 12.

Figure 11:
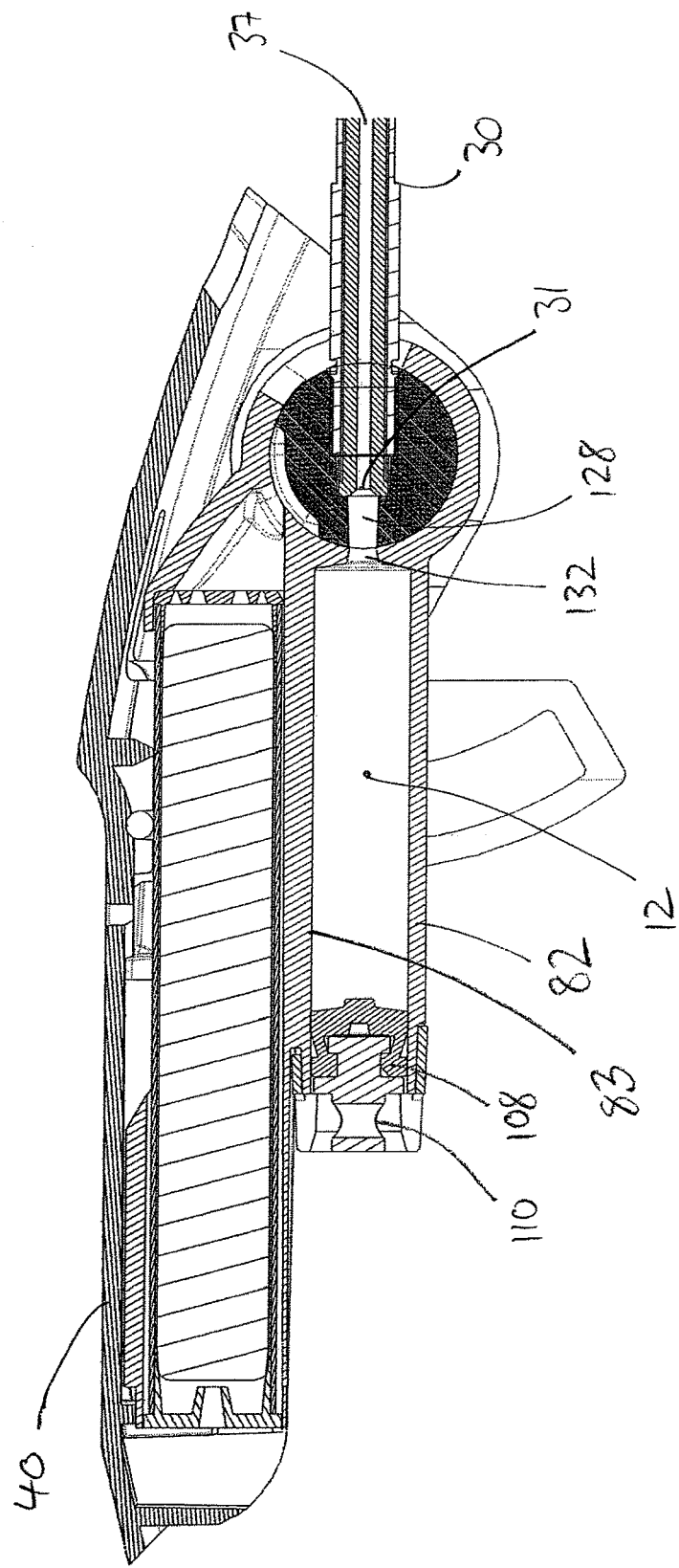
FIG. 11 is a cross-section from the right hand side showing the valve of the transfer assembly in the third transfer position.

Once the fluid 12 is released from the container 42, it is directed to the dispensing chamber 82. As shown in FIGS. 6, 7 and 11, a valve 120 is positioned between the container 42 and the dispensing chamber 82.

The valve 120 comprises an outer valve body 122 and an inner valve member 124. The valve member 124 is a cylinder with a cylindrical surface and axial ends. The valve body 122 is annular and encircles the valve member 124. The valve member 124 is attached to the housing 20 at its axial ends and the valve body 122 is attached to the transfer assembly 40. In this way the valve member 124 acts as a pivot around which the valve body 122 and transfer assembly 40 rotates when the transfer assembly 40 moves between the first transfer position (see FIG. 6), second transfer position and third transfer position (see FIG. 11).

A transfer channel 126 is defined by the valve member 124 as a channel on its cylindrical surface. The valve member 124 further defines a dispensing channel 128 a diametrical channel through the valve member 124.

The valve body 122 defines a container holder opening 130 which is in fluid communication with the container holder 44. The valve body 122 also defines a dispensing chamber opening 132 which is in fluid communication with the dispensing chamber 82.

When the transfer assembly 40 is in the second transfer position, the transfer channel 126 is aligned with the container holder opening 130 and the dispensing chamber opening 132 to provide a fluid path between the container holder opening 130 and the dispensing chamber opening 132. In this way, fluid 12 released from the container 42 may flow from the container holder 44 to the dispensing chamber 82 when the transfer assembly 40 is in the second transfer position.

Figure 8:
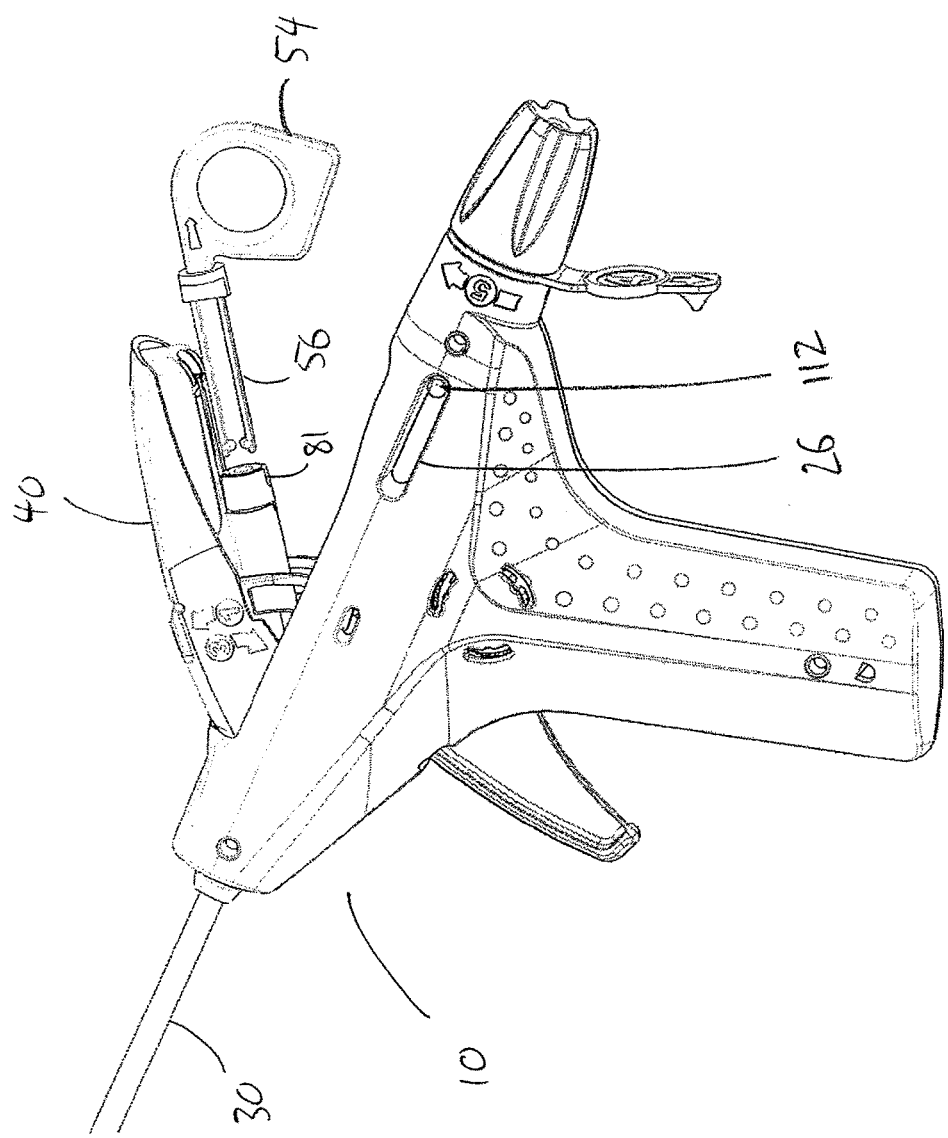
FIG. 8 is a view of the surgical instrument from the left hand side with the pull member disengaged from the dispensing chamber.

Before the surgical instrument 10 is used, a sealing disc 108 is located at a distal end of the dispensing chamber 82. To draw the released fluid 12 through the transfer channel 126 from the container holder 44 when the transfer assembly 40 is in the second transfer position, the sealing disc 108 is retracted proximally in the dispensing chamber 82. A pull member 54 is releasably attached to the sealing disc 108 to allow the user to retract the sealing disc 108. As shown in FIG. 3, when the transfer assembly 40 is in the first transfer position, the pull member 54 is restrained from movement by the housing 20. When the transfer assembly 40 is moved from the first transfer position to the second transfer position and the holder section 52 is moved to an angle of approximately 35° to the longitudinal axis 34, the pull member 54 moves above the housing 20 so that it is no longer restrained and can be operated. As shown in FIG. 3, before the pull member is operated, it is located in a position which prevents the transfer assembly 40 from being moved from the second transfer position to the third transfer position Once all the fluid 12 has been drawn into the dispensing chamber 82 and the sealing disc 108 is fully retracted, the pull member 54 disengages from the sealing disc 108. The pull member comprises two fingers 56 which engage a recess 110 on the sealing disc 108 so that the sealing disc 108 may be retracted. The recess 110 is in the form of a through-hole. The fingers 56 may be retained in the recess 110 by the inner surface 83 of the dispensing chamber 82. At its proximal end, the dispensing chamber defines two slots 81 (shown in FIG. 8) which allow the fingers 56 to disengage from the circumferential groove 110 when the sealing disc 108 is fully retracted. In this way, the pull member 54 is disengaged and separated from the dispensing chamber 82 (as shown in FIG. 8) and is then discarded. The transfer assembly 40 is now moveable from the second transfer position to the third transfer position.

Figure 9:
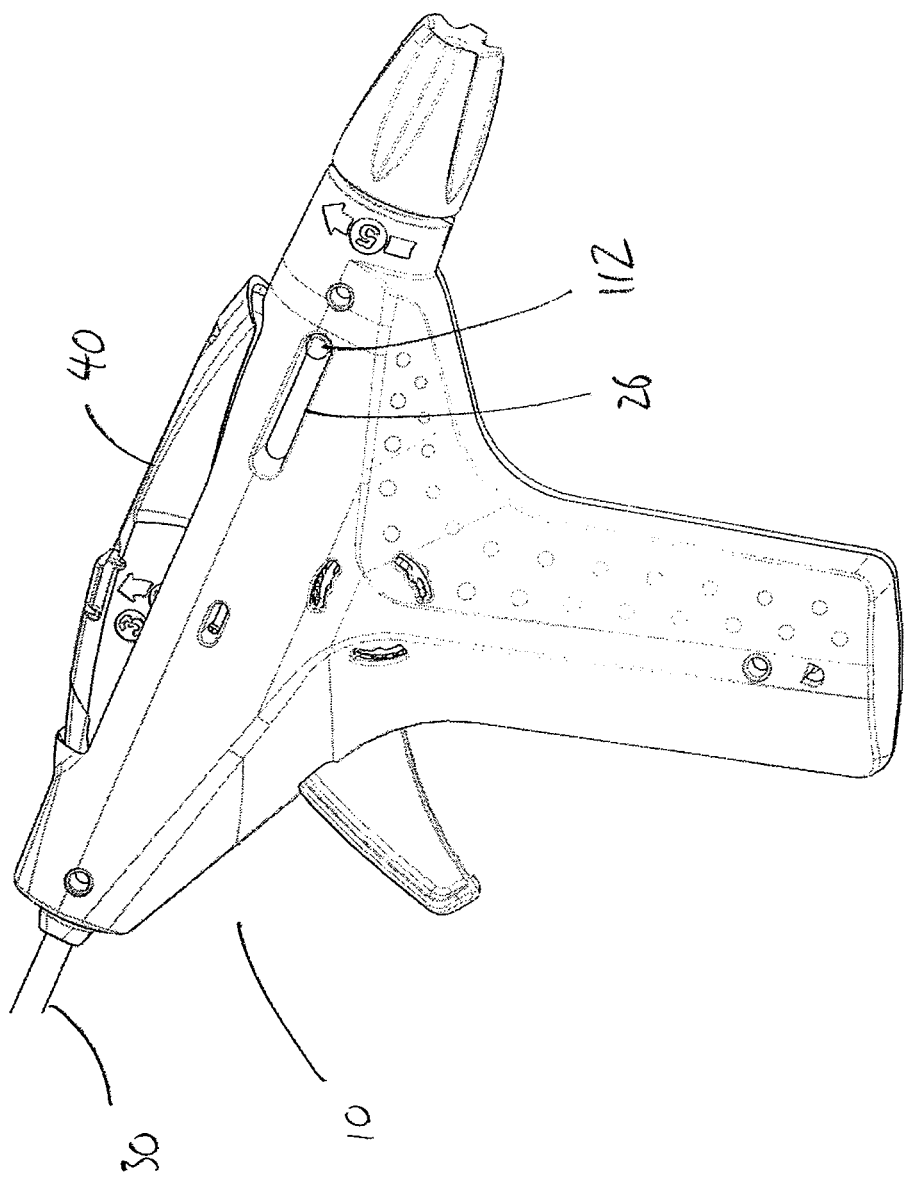
FIG. 9 is a view of the surgical instrument from the left hand side with the transfer assembly in the third transfer position.
Figure 10:
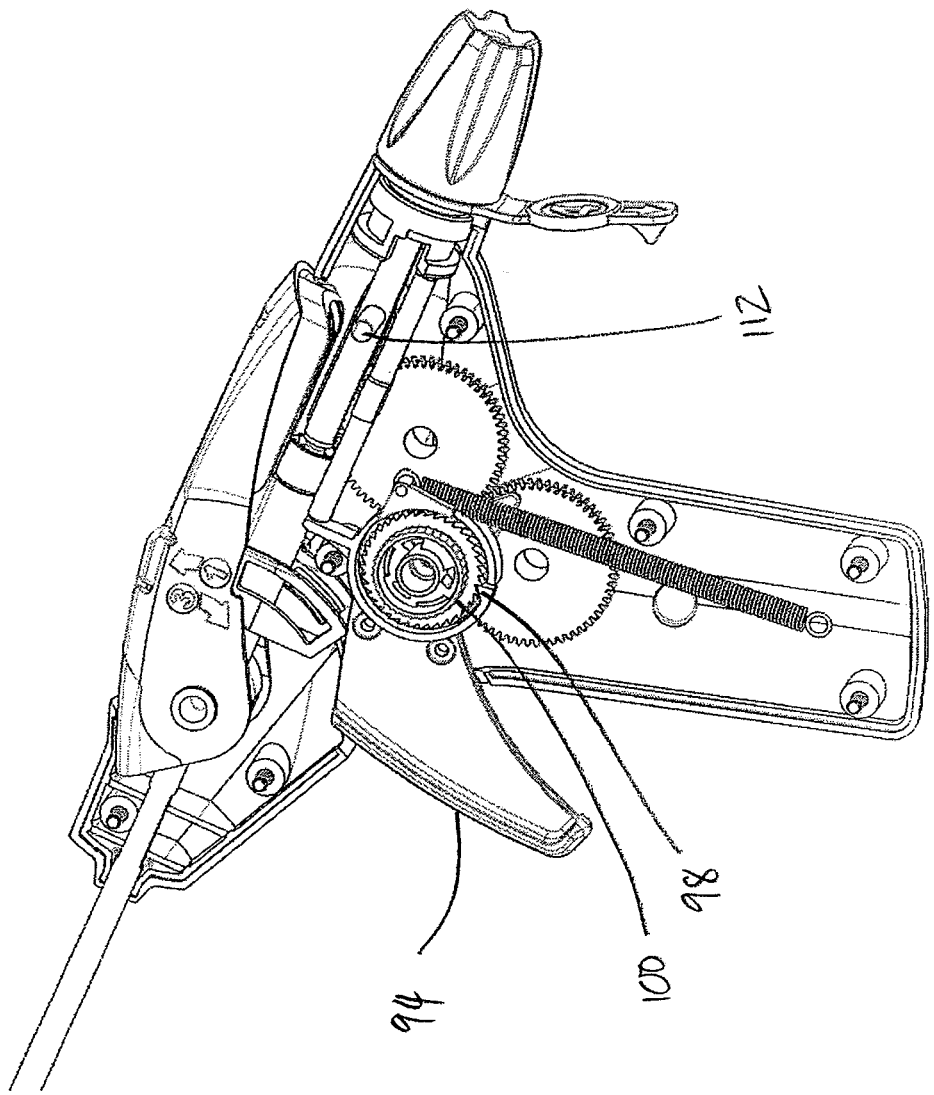
FIG. 10 is a similar view to FIG. 9 with the left hand side of the housing removed'

After the pull member 54 is discarded, the sealing disc 108 is fully retracted and the dispensing chamber 82 contains the fluid 12 to be dispensed. The transfer assembly 40 may then be moved to the third transfer position as shown in FIGS. 9 to 11. To reach the third transfer position, the transfer assembly 40 is pivoted about the valve member 124 until the dispensing chamber opening 132 is aligned with the dispensing channel 128 as shown in FIG. 11.

When the transfer assembly 40 is in the third transfer position, the sealing disc 108 is aligned with a plunger 84 as shown in FIG. 14.

As shown in FIGS. 12 to 16, the surgical instrument 10 further comprises a priming assembly 60. The priming assembly 60 includes a priming actuator 62 which is operable to drive the priming assembly 60. The priming actuator 62 is rotatably mounted to a proximal end of the housing 20. The priming actuator 62 is rotatable from a first priming position shown in FIG. 14 to a second priming position shown in FIG. 15.

The priming assembly 60 includes a safety element which is moveable from an engaged position to a disengaged position and which prevent the priming assembly 60 from being operated when it is in the engaged position. The safety element is in the form of a pull tab 64 attached to the priming actuator 62. In its engaged position (as shown in FIG. 14) the pull tab 64 engages a recess 28 on the housing 20 to prevent the priming actuator 62 from being operated. The pull tab 64 is separable from the priming actuator 62 so that in its disengaged position, the pull tab 64 is separated from the priming actuator 62 to allow the priming actuator 62 to be operated.

When the priming actuator 62 is rotated from the first priming position to the second priming position, the plunger 84 advances and pushes the sealing disc 108 distally within the dispensing chamber 82 to push the fluid 12 through the dispensing chamber opening 132 and the dispensing channel 128. The proximal end 31 of the dispensing shaft 30 is received within the valve member 124 and the through bore 37 is connected to the dispensing channel 128. Therefore fluid 12 pushed through the dispensing channel 128 may travel distally along the through bore 37 and be dispensed from the dispensing opening 33 at the distal end 32 of the dispensing shaft 30.

Figure 15:
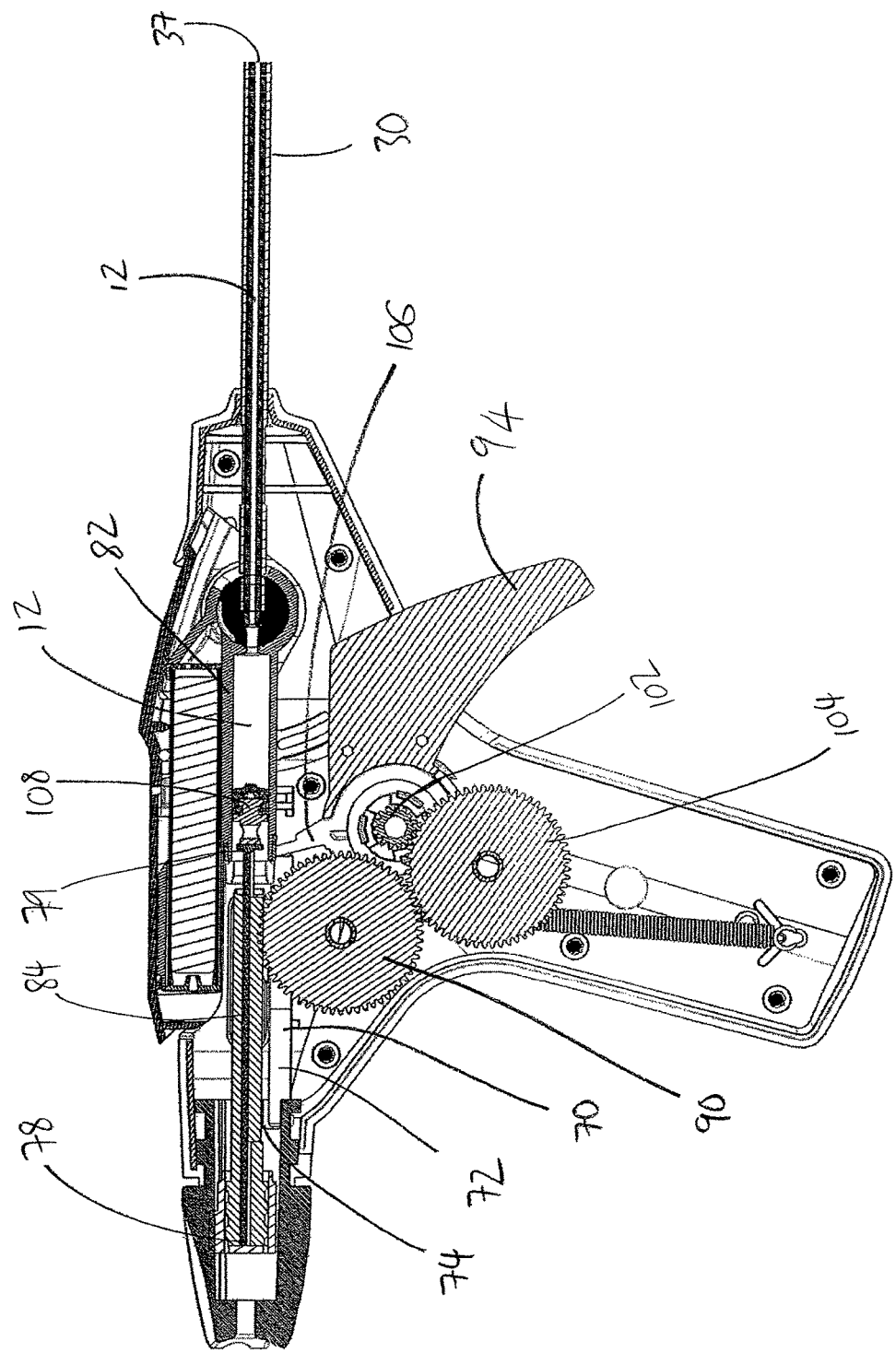
FIG. 15 is a cross-section of the surgical instrument from the right hand side showing the priming assembly in the second priming position.

Rotation of the priming actuator 62 from the first priming position to the second priming position rotates a priming cap 66 with an internal screw thread 65. The priming cap 66 is linearly moveable with respect to the priming actuator 62 by the engagement of a spline feature 67 on the priming cap 66 with a groove 63 on the priming actuator 62. The internal screw thread 65 on the priming cap 66 engages a complementary screw thread 87 mounted on a plunger drive assembly 86. The priming cap 66 is connected to a proximal end 78 of the plunger 84. In this way, rotation of the priming actuator 62 causes the internal screw thread 65 on the priming cap 66 to advance along the complementary screw thread 87 on the plunger drive assembly 86. Since the plunger 84 is connected to the priming cap 66, the plunger 84 will advance distally with respect to the plunger drive assembly 86 as shown in FIGS. 14 and 15. The advancement of the plunger 84 primes the through bore 37 of the dispensing shaft 30 with fluid 12 by advancing the sealing disc 108 in the dispensing chamber 82 and urging the fluid 12 out of the dispensing chamber 82.

Figure 12:
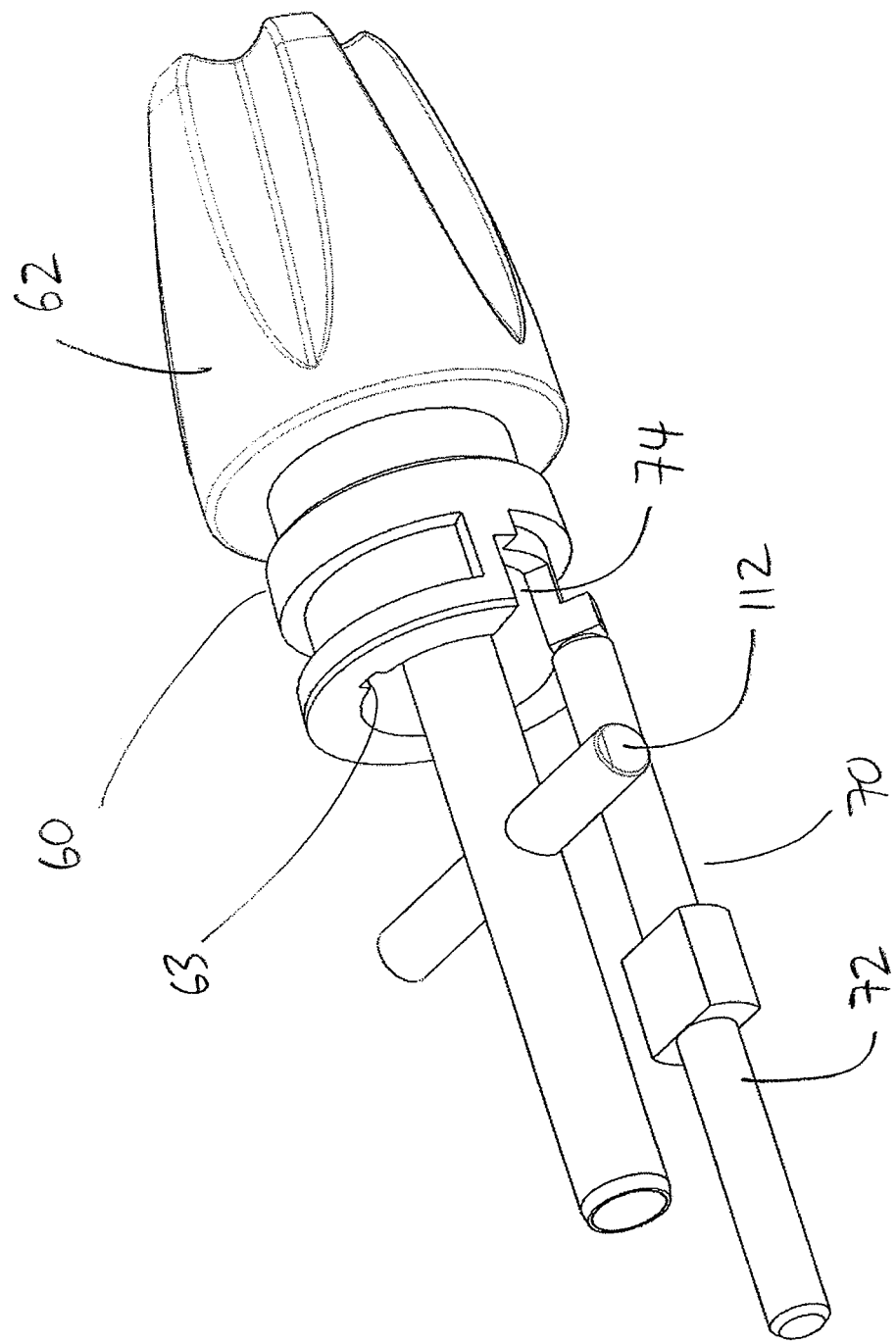
FIG. 12 is a view of the priming assembly from the left hand side.

The priming assembly 60 includes an interlock 70 as shown in FIGS. 12, 14 and 15. The interlock 70 is moveable from a locked configuration in which it prevents the dispensing assembly 80 from being operated to a released configuration in which the dispensing assembly 80 is operable. The interlock 70 is only moveable to the released configuration once the priming actuator 62 is in the second priming position. An advantage of the interlock 70 is that accidental operation of the dispensing assembly 80 is not possible until the priming assembly 60 has been operated and the priming actuator 62 is in the second priming position.

Figure 13:
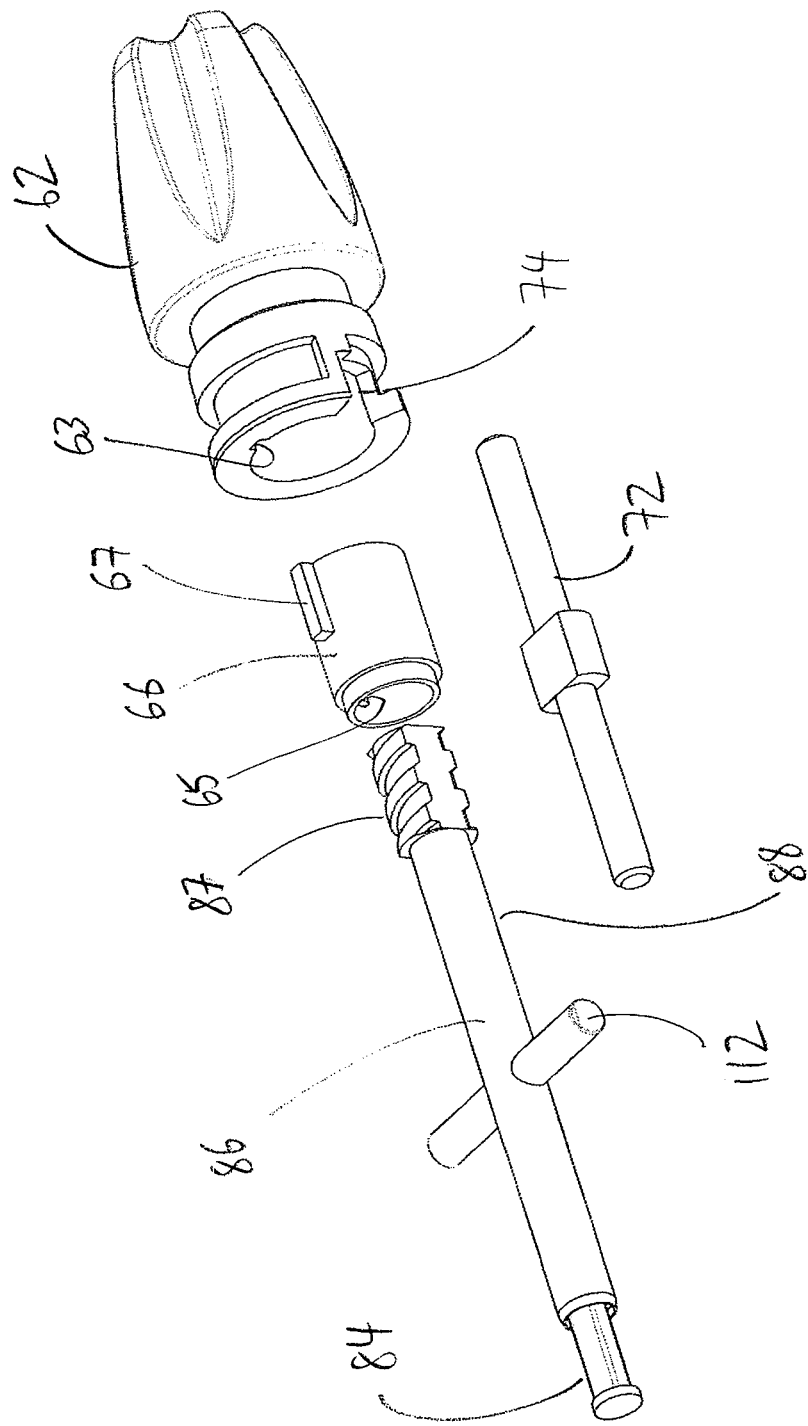
FIG. 13 is an exploded view of FIG. 12.

As shown in FIGS. 12 and 13, the interlock 70 includes a locking member 72. The locking member is elongate and is slidably mounted in the housing 20 to contact a locking formation 106 on the dispensing assembly 80 (see FIGS. 14 and 15) and to contact the priming actuator 62. When the priming actuator 62 is in the first priming position and the interlock 70 is in the locked configuration, the locking member 72 is unable to move and locks the trigger 94 in the second trigger position by contact with the locking formation 106.

The priming actuator 62 includes an interlock recess 74 positioned so that when the priming actuator 62 is in the second priming position, the interlock recess 74 is aligned with the locking member 72 to allow the locking member 72 to move into the interlock recess 74. The spring 96 exerts a force on the trigger 94 which causes the locking formation 106 to move the locking member 72 into the interlock recess 74 and this released configuration allows the trigger 94 to move from the second trigger position to the first trigger position. Once the trigger 94 is in the first trigger position, it is operable by the user.

As shown in FIGS. 11, 14 and 15, the dispensing assembly 80 comprises a dispensing chamber 82. The fluid 12 is held in the dispensing chamber 82 before it is moved into the dispensing shaft 30. The elongate plunger 84 is positioned to advance or retract within the dispensing chamber 82. When the plunger 84 is advanced within the dispensing chamber 82, the fluid 12 is urged out of the dispensing chamber 82 and into the through bore 37 of the dispensing shaft 30. The plunger advances within the dispensing chamber 82 in a distal direction. Fluid 12 urged out of the dispensing chamber 82 enters the through bore 37 of at the proximal end 31 of the dispensing shaft 30.

The plunger 84 has a distal end 79 which abuts against a sealing disc 108 which engages the internal surface 83 of the dispensing chamber 82 to form a seal. Advancement of the plunger 84 advances the sealing disc 108 within the dispensing chamber 82.

As shown in FIGS. 13, 14 and 15, the plunger 84 is connected to a plunger drive assembly 86 which includes a rack 88 and pinion gear wheel 90. The pinion gear wheel 90 is mounted within the housing 20. Turning the pinion gear wheel 90 engages the rack 88 to advance or retract the plunger 84. When the plunger 84 advances the sealing disc 108 is pushed along the dispensing chamber 82. Retraction of the plunger 84 will not cause the sealing disc 108 to move because the plunger 84 abuts the sealing disc 108 instead of being physically connected to the sealing disc 108.

The dispensing assembly 80 comprises a dispensing actuator 92 which is operable to drive the dispensing assembly 80. The dispensing actuator 92 is connected by an intermediate gear wheel 104 to the pinion gear wheel 90 of the plunger drive assembly 86.

Figure 16:
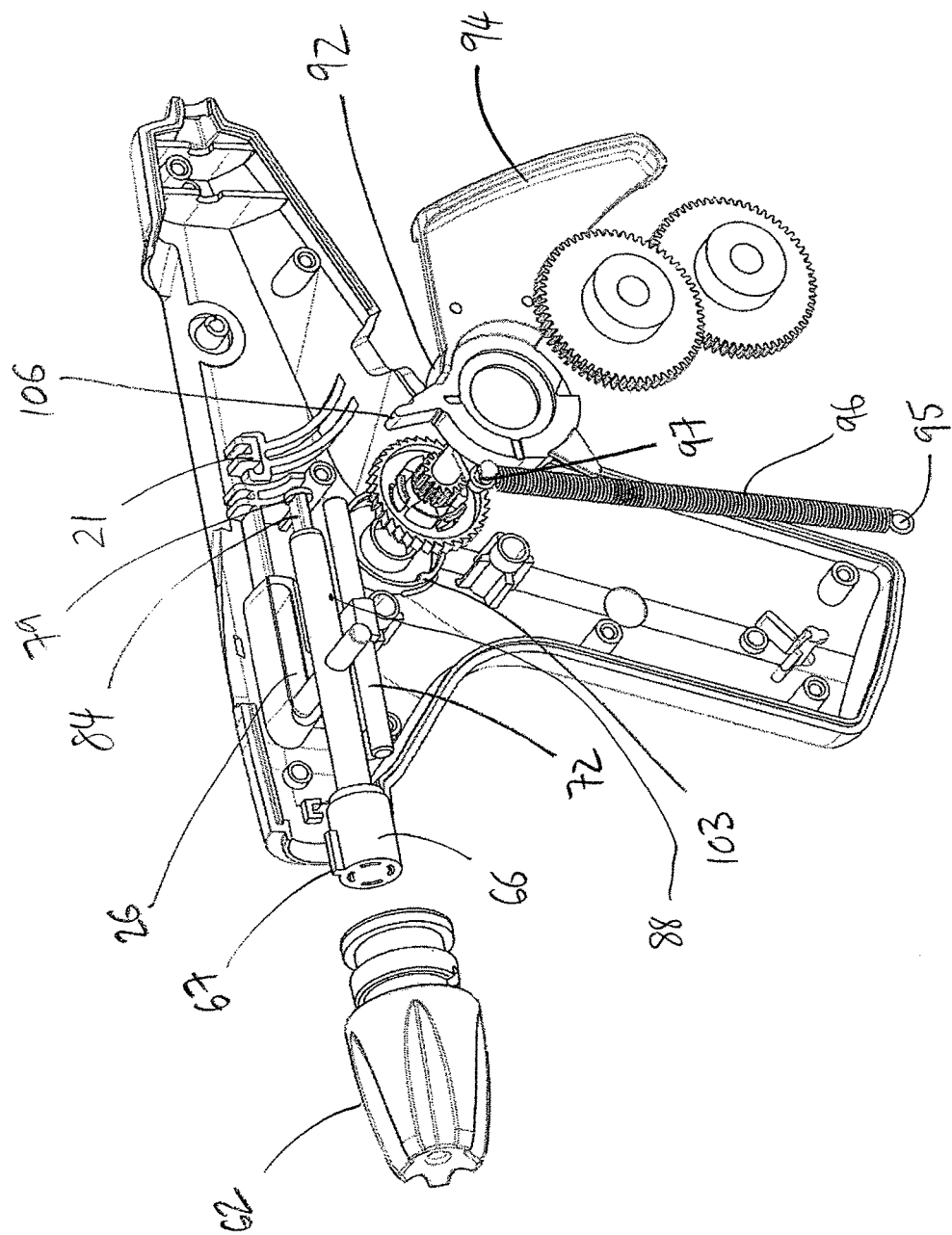
FIG. 16 is an exploded view of the dispensing assembly from the right hand side.

As shown in FIGS. 14, 15 and 16 the dispensing actuator 92 includes a reciprocable trigger 94 mounted to the housing 20 between the handle 22 and the body 24 of the housing 20. The trigger 94 is operable by a user's finger from a first trigger position to a second trigger position. The trigger 94 is biased by a spring 96 to return to the first trigger position when the user's finger is released at the second trigger position. The spring 96 is attached to the housing 20 at a first end 95 and attached to the dispensing actuator 92 at a second end 97.

Figure 18A:
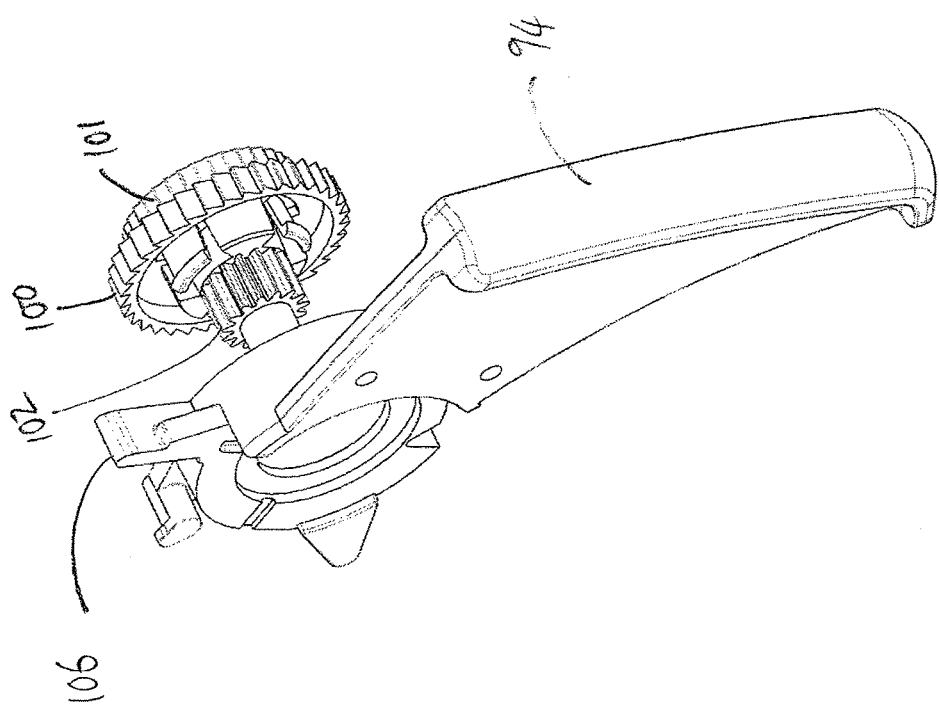
FIG. 18A is a view of the trigger from above the right hand side.
Figure 18B:
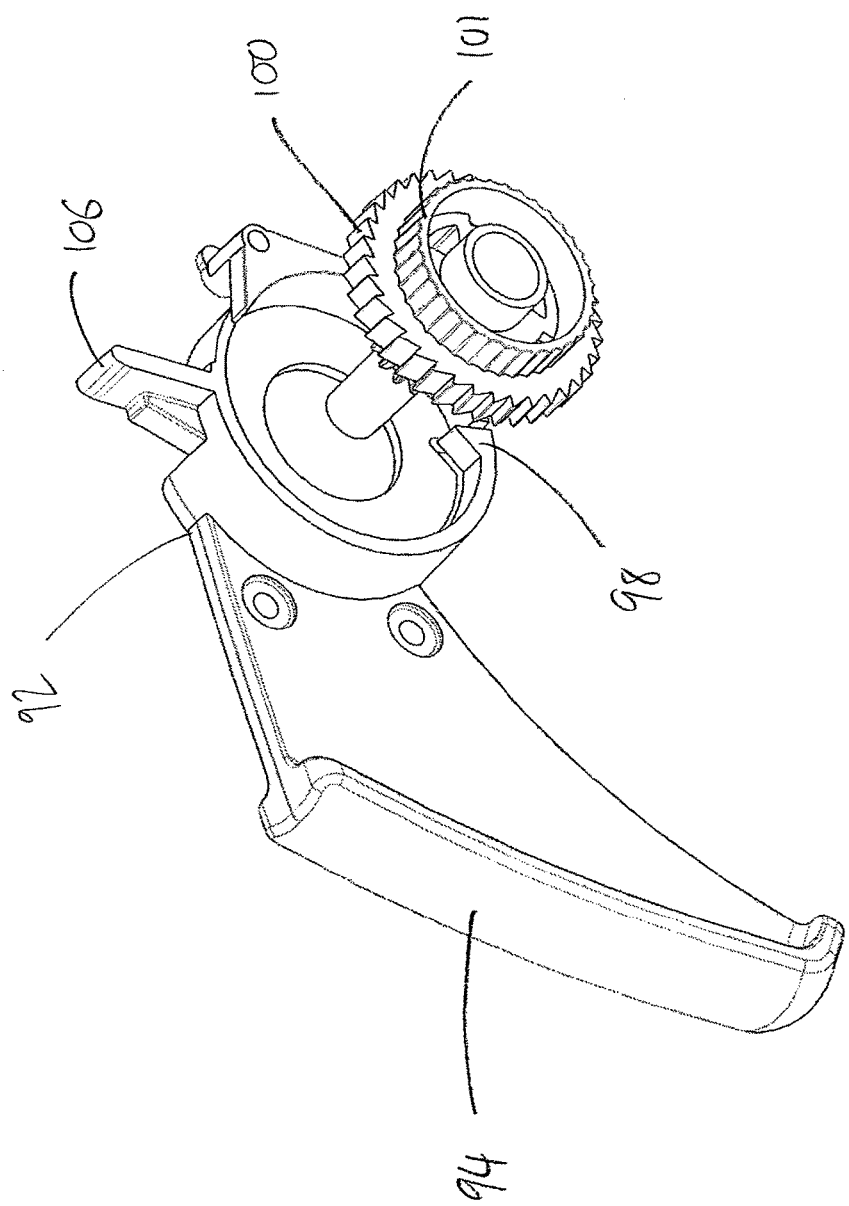
FIG. 18B is a view of the trigger from the left hand side.

As shown in FIGS. 18A and 18B, a pawl 98 is moulded into the trigger 94 and a ratchet 100 is connected to a trigger gear wheel 102. When the trigger 94 is moved from the first trigger position to the second trigger position the pawl 98 engages the ratchet 100 to turn the trigger gear wheel 102.

When the trigger 94 is moved from the second trigger position to the first trigger position the pawl 98 and ratchet 100 disengage so that the trigger gear wheel 102 does not turn.

As shown in FIGS. 14 and 15, turning the trigger gear wheel 102 will turn the intermediate gear wheel 104 to turn the pinion gear wheel 90 to advance the plunger 84. The relative sizes of the trigger gear wheel 102, intermediate gear wheel 104 and pinion gear wheel 90 are chosen to provide an overall gear ratio between the trigger gear wheel 102 and the pinion gear wheel 90 of 4 to 1. Therefore a 10° rotation of the trigger 94 results in a 2.5° rotation of the pinion gear wheel 90. The size of the pinion gear wheel 90 is chosen to advance the rack 88 by a predetermined amount when the trigger 94 is operated from the first trigger position to the second trigger position. This will cause the plunger 84 to advance by a predetermined amount to dispense a predetermined volume of the fluid 12 from the dispensing opening 33 of the surgical instrument 10.

Figure 17A:
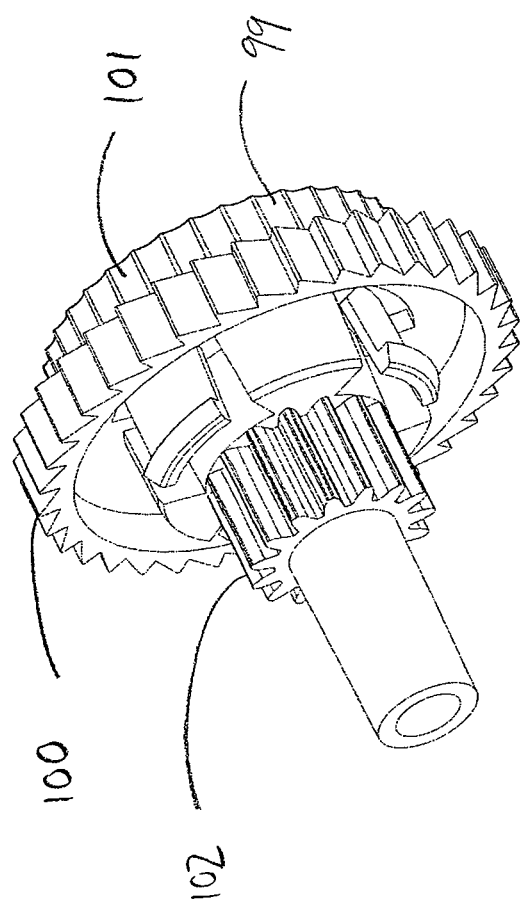
FIG. 17A is a view of the trigger gear wheel from the right hand side.
Figure 17B:
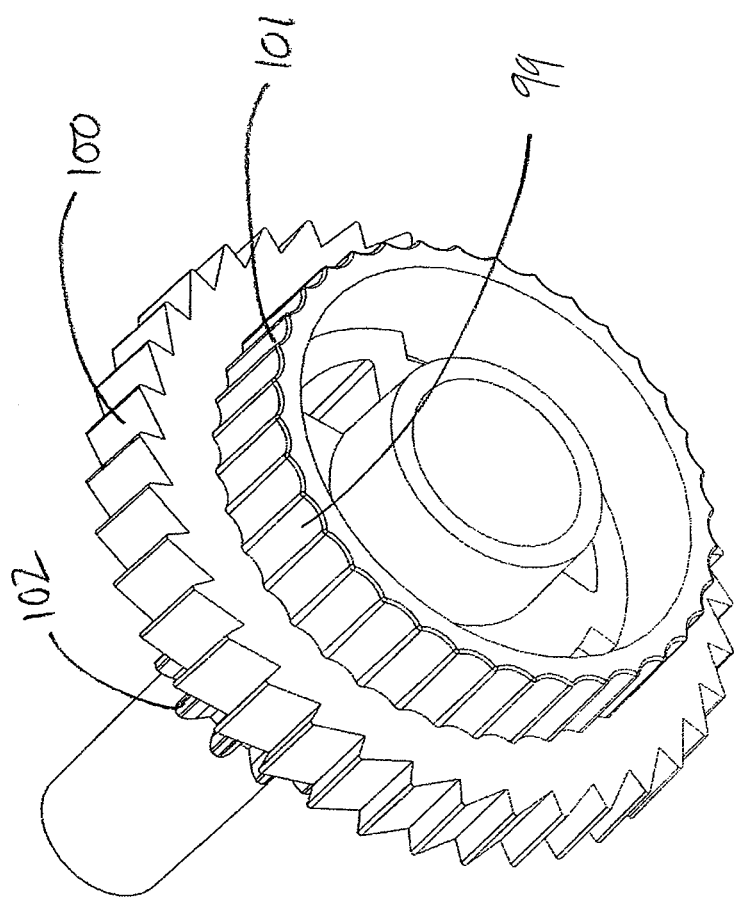
FIG. 17B is a view of the trigger gear wheel from the left hand side.

As shown in FIGS. 17A and 17B an indexing wheel 101 is attached to the trigger gear wheel 102. The indexing wheel 101 enables the movement of the trigger 94 between the first trigger position and the second trigger position to be indexed. The indexing wheel 101 includes indentations 99 on its circumference which engage an indexing formation 103 on the housing 20 (see FIG. 16) to provide the indexing. The engagement of the indentations 99 with the indexing formation 103 also provides an additional frictional force on the ratchet 100 to assist the trigger 94 to move from the second trigger position to the first trigger position without moving the ratchet 100.

The surgical instrument 10 dispenses the fluid 12 in discrete doses. A single dose is known as a delivery and each delivery is a predetermined volume of fluid 12. The internal diameter of the inner surface 83 of the dispensing chamber 82 is chosen to be 7 mm so that advancement of the plunger 84 by a set distance of 0.65 mm will dispense a predetermined volume of approximately 25 mm$^3$.

The surgical instrument 10 is capable of dispensing a predetermined number of deliveries which is 35 deliveries. After the dispensing actuator 92 has been operated 35 times, a hard stop on the dispensing assembly 80 prevents the dispensing actuator 92 from being operated again. The hard stop is provided by a stop projection 112 on the plunger drive assembly 86 (as shown in FIG. 13) engaging the housing 20.

As shown in FIGS. 9 and 16, the stop projection 112 is moveable within a slot 26 on the housing 20. The slot 26 is in an exterior surface of the housing 20 so that the stop projection 112 is visible to the user of the surgical instrument 10. The stop projection 112 advances in the slot 26 as the plunger 84 advances the sealing disc 108 in the dispensing chamber 82. The hard stop is provided by the stop projection 112 reaching a distal end of the slot 26. The slot 26 is located so that the stop projection 112 reaches the distal end of the slot 26 when the predetermined number of 35 deliveries is reached.

By being visible to the user, the relative position of the stop projection 112 in the slot may provide a visual indication of the number of deliveries the surgical instrument 10 has made.

Use of the surgical instrument 10 in a hernia mesh fixation procedure will now be described.

The fluid 12 is a cyanoacrylate adhesive suitable for securing a hernia mesh in place at the operative site in the human or animal body. The hernia mesh is secured in place by a number of deliveries of adhesive from the surgical instrument 10. Each delivery of adhesive has a similar function to a suture or tack. The hernia mesh is secured in place by approximately 25 deliveries of adhesive. Since the predetermined maximum number of deliveries of the device is 35 deliveries, there are approximately 10 extra deliveries of adhesive available for the surgeon to use as necessary. The surgeon may use some of these extra deliveries for closure of the peritoneum if appropriate.

The detailed sequence of the steps for using the surgical instrument 10 is as follows. In this description, it is assumed that a scrub nurse and a surgeon will be present during the procedure but the surgical instrument 10 may also be prepared and used by a single person.

The surgical instrument 10 is provided in sterile packaging with the transfer assembly 40 in the first transfer position at an angle of 25° to the longitudinal axis 34 of the dispensing shaft 30. The scrub nurse removes the surgical instrument 10 from the packaging and moves the transfer assembly 40 to the second transfer position at an angle of 35° to break the frangible glass container 42 within the container holder 44. The move to the second transfer position aligns the dispensing chamber 82 and the container holder 44 with the transfer channel 126 on the valve 120. Next the scrub nurse retracts the sealing disc 108 in the dispensing chamber 82 by pulling the pull member 54 which draws the adhesive fluid 12 into the dispensing chamber 82. The fluid 12 passes through the filter 46 and any container fragments are retained by the filter 46 and separated from the fluid 12. The pull member 54 is disengaged from the sealing disc 108 at the end of its travel and is discarded.

The scrub nurse then moves the transfer assembly 40 to the third transfer position (as shown in FIGS. 9, 10 and 11) which moves the dispensing chamber 82 from alignment with the transfer channel 126 of the valve 120 to alignment with the dispensing channel 128.

At this stage, the transfer sequence has been completed and the priming sequence can be started. To start the priming sequence the scrub nurse removes the safety element 64 which releases the priming actuator 62. Next the scrub nurse rotates the priming actuator 62 which advances the plunger 84 to push the sealing disc 108 forward distally in the dispensing chamber 82 which in turn pushes adhesive fluid 12 through the dispensing channel 128 of the valve 120 and along the through bore 37 of the dispensing shaft 30 to near the dispensing opening 33 of the surgical instrument 10. Once the priming actuator 62 has been rotated 320° from the first priming position to the second priming position, the locking member 72 of the interlock 70 is pushed backwards into the interlock recess 74 on the priming actuator 62 by the force of the spring 96 on the dispensing actuator 92. This causes the trigger 94 to be released to the first trigger position which completes the priming sequence and the surgical instrument 10 is now ready for use.

The scrub nurse hands the surgical instrument 10 to the surgeon to use. When the surgeon uses a finger to pull the trigger 94 from the first trigger position to the second trigger position, the plunger drive assembly 86 advances the plunger 84 to make a delivery of fluid adhesive 12 from the dispensing opening 33. When the surgeon releases the trigger 94 the dispensing actuator 92 is rotated by the spring 96 from the second trigger position back to the first trigger position without the ratchet 100 rotating, ensuring that the plunger 84 remains stationary. The Surgeon uses up to 25 deliveries of adhesive fluid 12 to attach the hernia mesh in the desired position.

The invention claimed is:

1. A surgical instrument for dispensing a fluid comprising:
a housing;
a dispensing shaft which is elongate and which has a proximal end and a distal end, wherein the proximal end of the dispensing shaft is received in the housing and the distal end defines a dispensing opening for dispensing the fluid and the dispensing shaft includes a through bore which extends along the dispensing shaft from the proximal end to the dispensing opening at the distal end;
a dispensing assembly connected to the housing, said dispensing chamber including a dispensing chamber which holds the fluid before it is dispensed, wherein the dispensing chamber is in fluid communication with the through bore of the dispensing shaft and the dispensing assembly is operable to move the fluid from the dispensing chamber along the through bore and dispense the fluid from the dispensing opening;
a container in which the fluid is stored before the surgical instrument is used;
a transfer assembly connected to the housing, said transfer assembly being operable via movement from a first transfer position to a second transfer position to open the container and transfer the fluid from a container holder to the dispensing chamber; and,
a pull member attached to a sealing disc, said pull member being operable to retract the sealing disc within the dispensing chamber for drawing the fluid from the container into the dispensing chamber when the transfer assembly is in the second transfer position, wherein said pull member is located in a position so that before it is operated and when the transfer assembly is in the first transfer position, said pull member is restrained from movement by the housing to prevent the pull member from being operated until the transfer assembly is in the second transfer position and the container has been opened.

2. A surgical instrument as claimed in claim 1 wherein the container is a frangible container.

3. A surgical instrument as claimed in claim 2 wherein the transfer assembly includes a filter which is positioned between the container and the dispensing chamber for retaining fragments of the frangible container which may be produced when the container is opened and separating the fragments from the fluid which is transferred to the dispensing chamber.

4. A surgical instrument as claimed in claim 1 wherein the transfer assembly is moveable to a third transfer position and the surgical instrument includes a valve which is positioned between the container and the dispensing chamber wherein in the second transfer position the valve allows fluid to flow from the container into the dispensing chamber and wherein in the third transfer position the valve allows fluid to flow from the dispensing chamber into the dispensing shaft.

5. A surgical instrument as claimed in claim 4 wherein the valve includes an outer valve body and an inner valve member, wherein the outer valve body is attached to the transfer assembly and the inner valve member is attached to the housing so that the outer valve body is rotatable around the inner valve member to allow the transfer assembly to rotate between the first transfer position, the second transfer position and third transfer position.

6. A surgical instrument as claimed in claim 5 wherein the inner valve member is cylindrical and the outer valve body is annular and encircles the inner valve member so that the inner valve member acts as a pivot around which the outer valve body and transfer assembly are rotatable.

7. A surgical instrument as claimed in claim 1 further comprising a plunger which abuts against the sealing disc which is slidably mounted within the dispensing chamber, wherein operation of the dispensing assembly causes the plunger to advance the sealing disc within the dispensing chamber to urge the fluid out of the dispensing chamber and along the through bore in the dispensing shaft.

8. A surgical instrument as claimed in claim 1 wherein the pull member includes disengageable fingers which engage the sealing disc so that when the pull member has been operated to retract the sealing disc within the dispensing chamber, the fingers are disengageable from the sealing disc to allow the pull member to be moved to a position which allows the transfer assembly to be moved from the second transfer position to a third transfer position.

9. A surgical instrument as claimed in claim 1 wherein the container is a glass container.

10. A surgical instrument as claimed in claim 1 wherein the fluid is an adhesive.

11. A surgical instrument as claimed in claim 10 wherein the adhesive is a cyanoacrylate.

12. A surgical instrument for dispensing a fluid comprising:
a housing;
a dispensing shaft which is elongate and which has a proximal end and a distal end, wherein the proximal end of the dispensing shaft is received in the housing and the distal end defines a dispensing opening for dispensing the fluid and the dispensing shaft includes a through bore which extends along the dispensing shaft from the proximal end to the dispensing opening at the distal end;
a dispensing assembly connected to the housing, said dispensing chamber including a dispensing chamber which holds the fluid before it is dispensed, wherein the dispensing chamber is in fluid communication with the through bore of the dispensing shaft and the dispensing assembly is operable to move the fluid from the dispensing chamber along the through bore and dispense the fluid from the dispensing opening;
a container in which the fluid is stored before the surgical instrument is used;
a transfer assembly connected to the housing, said transfer assembly being operable via movement from a first transfer position to a second transfer position to open the container and transfer the fluid from a container holder to the dispensing chamber; and, wherein the transfer assembly is moveable to a third transfer position and the surgical instrument includes a valve which is positioned between the container and the dispensing chamber wherein in the second transfer position the valve allows fluid to flow from the container into the dispensing chamber and wherein in the third transfer position the valve allows fluid to flow from the dispensing chamber into the dispensing shaft, the valve further including an outer valve body and an inner valve member, wherein the outer valve body is attached to the transfer assembly and the inner valve member is attached to the housing so that the outer valve body is rotatable around the inner valve member to allow the transfer assembly to rotate between the first transfer position, the second transfer position and the third transfer position, wherein the inner valve member is cylindrical and the outer valve body is annular and encircles the inner valve member so that the inner valve member acts as a pivot around which the outer valve body and the transfer assembly are rotatable.

13. A surgical instrument as claimed in claim 12 wherein the container is a frangible container.

14. A surgical instrument as claimed in claim 13 wherein the transfer assembly includes a filter which is positioned between the container and the dispensing chamber for retaining fragments of the frangible container which may be produced when the container is opened and separating the fragments from the fluid which is transferred to the dispensing chamber.

15. A surgical instrument as claimed in claim 12 wherein the container is a glass container.

16. A surgical instrument as claimed in claim 12 wherein the fluid is an adhesive.

17. A surgical instrument as claimed in claim 16 wherein the adhesive is a cyanoacrylate.

* * * * *